US007678545B2

(12) United States Patent
Abbott et al.

(10) Patent No.: US 7,678,545 B2
(45) Date of Patent: Mar. 16, 2010

(54) POLYELECTROLYTE MULTILAYER FILMS AT LIQUID-LIQUID INTERFACES AND METHODS FOR PROVIDING AND USING SAME

(75) Inventors: Nicholas Abbott, Madison, WI (US); Nathan A. Lockwood, Minneapolis, MN (US); Katie D. Cadwell, Madison, WI (US); Frank Caruso, Melbourne (AU); Elvira Tjipto, Melbourne (AU)

(73) Assignee: Wisconsin Alumni Research Foundation, Madison, WI (US)

( * ) Notice: Subject to any disclaimer, the term of this patent is extended or adjusted under 35 U.S.C. 154(b) by 505 days.

(21) Appl. No.: 11/483,891

(22) Filed: Jul. 10, 2006

(65) Prior Publication Data

US 2009/0023155 A1 Jan. 22, 2009

Related U.S. Application Data

(60) Provisional application No. 60/697,432, filed on Jul. 8, 2005.

(51) Int. Cl.
*G01N 33/53* (2006.01)

(52) U.S. Cl. .................................................... 435/7.1

(58) Field of Classification Search ....................... None
See application file for complete search history.

(56) References Cited

U.S. PATENT DOCUMENTS 4,948,506 A * 8/1990 Lonsdale et al. ............ 210/490
7,041,304 B2 * 5/2006 Ju et al. ...................... 424/401
2002/0052002 A1 * 5/2002 Niehaus et al. .............. 435/7.1

FOREIGN PATENT DOCUMENTS

EP 1116516 A 7/2001

OTHER PUBLICATIONS

Slevin et al. [Electrochemical Characterization of Polyelectrolyte Multilayers Deposited at Liquid-Liquid Interfaces, Langmuir 2003, 19, 1287-1294].*

Slevin, et al. Electrochemical characterization of polyelectrolyte multilayers deposited at liquid-liquid interfaces, Langmuir (2003) 19: 1287-1294 (American Chemical Society).

International Search Report for PCT/US2006/026530, Patent Cooperation Treaty, mailed Mar. 23, 2009.

* cited by examiner

*Primary Examiner*—Ann Y Lam
(74) *Attorney, Agent, or Firm*—Quarles & Brady, LLP

(57) ABSTRACT

The present invention is directed to methods for providing a polyelectrolyte multilayer film at a liquid-liquid interface. Such methods include steps of sequentially-depositing layers of cationic and anionic polyelectrolytes at a liquid-liquid interface that is formed between immiscible first and second liquids whereby a polyelectrolyte multilayer film is provided at the liquid-liquid interface. In certain preferred embodiments, the first liquid is an aqueous solution and the second liquid is a liquid crystal. In alternative embodiments, the first liquid is an aqueous solution and the second liquid is an oil. The invention further encompasses polyelectrolyte multilayer films provided by the disclosed methods as well as applications utilizing such materials.

11 Claims, 16 Drawing Sheets

A B

A B

A

5CB

PAH

PAA

FITC-PAH

B

PSS

Methacryloxyethyl thiocarbamoyl rhodamine B

A

B

D-Glucuronic acid N-acetyl glucosamine

POLYELECTROLYTE MULTILAYER FILMS AT LIQUID-LIQUID INTERFACES AND METHODS FOR PROVIDING AND USING SAME

CROSS-REFERENCE TO RELATED APPLICATION

The present utility patent application claims the benefit of U.S. Provisional 60/697,432, filed Jul. 8, 2005, which is incorporated by reference herein in its entirety.

STATEMENT REGARDING FEDERALLY SPONSORED RESEARCH

This invention was made with United States government support awarded by the National Science Foundation—Grant Nos. CTS-0327489 and DMR-0079983. The United States has certain rights in this invention.

FIELD OF THE INVENTION

This invention relates generally to methods of functionalizing liquid-liquid interfaces. More particularly, the present invention is directed to polyelectrolyte multilayer films formed at liquid-liquid interfaces and methods for providing and using the same.

BACKGROUND OF THE INVENTION

The layer-by-layer technique of sequential adsorption of oppositely charged polymers and nanoparticles onto solid surfaces has been demonstrated in the past to be a simple and versatile method for the fabrication of supported thin films. The method creates polyelectrolyte multilayer (PEM) films by alternately immersing the surface of a solid into solutions of polycations or polyanions. The layer-by-layer technique can be used to deposit many types of polymers, molecules and particulates onto surfaces, including synthetic, linear polyelectrolytes; dendrimers; charged biomolecules such as polynucleotides, proteins and polysaccharides; or polyvalent small molecular weight organic compounds. The diverse nature of these materials (including nanoparticles) has made possible the use of the method in the fabrication of ion-selective membranes, chemical sensors, systems for drug and gene delivery, and patterned surfaces. It has also been demonstrated that it is possible to incorporate non-ionic polymers into multilayer films by the layer-by-layer method, and such non-ionic polymers fall within the scope of materials that can be deposited at liquid-liquid interfaces by the methods described in this invention.

The process of PEM formation and the physical properties of the resulting films (e.g., morphology, thickness, layer interpenetration) depend on the deposition procedure, the chemical structure and molecular weight of the polyelectrolytes, and the ionic strength and pH of the deposition solution. PEM films are most often prepared on flat solid substrates, but have also been formed on suspended colloidal particles and the surfaces of macroscopic three-dimensional objects. Methods of forming PEM films on solids have typically used either (i) solids with hydrophobic interfaces in conjunction with a polyelectrolyte that partitions on hydrophobic substrates or (ii) solids with charged surfaces to initiate PEM film formation.

In contrast, the preparation of PEM films at interfaces between liquid-liquid phases is largely an unexplored field. However, there are various reasons why preparation of PEM films at liquid-liquid interfaces, if possible, would be of great industrial value. For example, in the context of aqueous-liquid crystal interfaces, the formation or reorganization of PEM films overlying a liquid crystal may result in ordering transitions in the liquid crystal thereby providing a facile means to amplify changes in the structure of PEM films into optical or electrical signals. Second, formation or reorganization of PEM films at a liquid-liquid interface may provide a general and versatile approach for adding functionality to liquid crystals for use as chemical and biological sensors or as materials on which biological cells can be cultured. These propositions build from the observation that the orientations assumed by liquid crystals near interfaces (the "anchoring" of the liquid crystal) are known to be highly sensitive to the nature of the interactions between the mesogens forming the liquid crystal and a confining interface. Depending on the structure of the interface, the liquid crystal may align normal to the interface (homeotropic anchoring), parallel to the interface (planar anchoring), or at an angle relative to the interface (tilted anchoring). Other orientational orderings of liquid crystals near interfaces are also known.

Past studies have reported on the influence of surfactants on the orientations of liquid crystals when the surfactants are adsorbed at interfaces of aqueous phases and thermotropic liquid crystals in emulsions (Drzaic, *Liquid Crystal Dispersions. Series on Liquid Crystals*; World Scientific: Singapore, 1995; Poulin et al. *Science* 1997, 275, 1770; Mondain-Monval et al. *Eur. Phys. J. B* 1999, 12, 167). More recently, planar interfaces between thermotropic liquid crystals and aqueous solutions have been used to investigate the orientations of liquid crystals decorated with surfactants (Brake et al. *Langmuir* 2002, 16, 6101; Brake et al. *Langmuir* 2003, 16, 6436; Brake et al. *Langmuir* 2003, 21, 8629), lipids (Brake et al. *Science* 2003, 302, 2094; Brake et al. *Langmuir* 2005, 21, 2218), and proteins (Brake et al. *Science* 2003, 302, 2094.).

The formation of PEMs at liquid-liquid interfaces may also be used to mechanically stabilize the interface or to immobilize agents such as catalysts of reactions at the interface. For example, if an enzyme is incorporated into a PEM at a liquid-liquid interface then the substrates and products of the enzymatic reaction could be delivered to and from the enzyme via either side of the PEM at the liquid-liquid interface. In addition, systems containing multiple enzymes could be hosted within PEMs formed at liquid-liquid interfaces. The capacity of the PEM to host the enzyme could be substantially greater than is possible when enzymes adsorb directly at liquid-liquid interfaces. In addition, the microenvironment of the enzyme can be controlled by the structure of the PEM, thus maximizing the activity and stability of the enzyme. The formation of PEMs at liquid-liquid interfaces could also be a general and facile route to the fabrication of free standing PEM structures when the liquids are chosen to be easily removed from the PEM. PEMs formed at liquid-liquid interfaces could also be used to prevent the adsorption of biomolecules and other molecules at liquid-liquid interfaces, thus preventing the fouling of the interface. PEMs formed at liquid-liquid interfaces may also change the rheological properties of the interfaces, which could find use in stabilizing emulsions and other dispersed liquid phases used in cosmetic formulations, drug delivery and other technologies of value to society.

It can therefore be appreciated from the foregoing that fabrication of PEM films in combination with liquid-liquid interfaces, if possible, would yield valuable materials with utility in a wide variety of applications.

SUMMARY OF THE INVENTION

In a first embodiment, the present invention is directed to methods for providing a polyelectrolyte multilayer film at a liquid-liquid interface. Such methods include steps of sequentially-depositing layers of cationic and anionic polyelectrolytes at a liquid-liquid interface that is formed between immiscible first and second liquids whereby a polyelectrolyte multilayer film is provided at the liquid-liquid interface. In certain preferred embodiments, the first liquid is an aqueous solution and the second liquid is a liquid crystal. In alternative embodiments, the first liquid is an aqueous solution and the second liquid is an oil. As well, one of the liquids may be in the form of a droplet such that the polyelectrolyte multilayer film is formed at the interface of droplet and surrounding liquid.

In another embodiment, the invention is directed to a polyelectrolyte multilayer film positioned at a liquid-liquid interface between two immiscible liquids. Such PEM films include sequentially-deposited layers of cationic and anionic polyelectrolytes wherein the polyelectrolyte multilayer film is positioned between immiscible first and second liquids. In preferred embodiments, the first liquid is an aqueous solution and the second liquid is a liquid crystal. In alternative embodiments, the first liquid is an aqueous solution and the second liquid is an oil. In certain other embodiments, the polyelectrolyte multilayer film contains non-ionic polymers in addition to the cationic and anionic polyelectrolytes.

In yet another embodiment, the invention encompasses a method for providing a polyelectrolyte multilayer film at an aqueous-liquid crystal interface. Such a method includes steps of sequentially-depositing layers of cationic and anionic polyelectrolytes at an aqueous-liquid crystal interface that is formed between an aqueous phase and a liquid crystal phase whereby a polyelectrolyte multilayer film is provided at the aqueous-liquid crystal interface. In preferred methods, the polyelectrolyte multilayer film includes an excipient capable of interacting with an analyte present in the aqueous solution thereby causing a change in orientational ordering of the liquid crystal. In particularly preferred embodiments, the excipient is a ligand or a receptor capable of selectively-binding the analyte. Alternatively, the excipient is a molecule capable of undergoing a chemical reaction in the presence of the analyte.

Certain embodiments are characterized by the polyelectrolyte multilayer film being deposited directly on the liquid crystal phase. Alternatively, methods according to the invention may include the additional step of seeding the aqueous-liquid crystal interface with a lipid comprising a charged head group wherein deposition of the polyelectrolyte multilayer film is facilitated by the lipid. As well, the liquid crystal may be in the form of a droplet such that the polyelectrolyte multilayer film is formed at the interface of liquid crystal droplet and surrounding aqueous phase.

Other embodiments of the invention encompass a modified aqueous-liquid crystal interface. Such an interface includes: (a) an aqueous phase; (b) a liquid crystal phase; and (c) a polyelectrolyte multilayer film positioned between the aqueous phase and the liquid crystal phase. Such embodiments may, optionally, encompass additional non-ionic polymers in the multilayer film formed at an aqueous-liquid crystal interface. Such materials may be formed by sequential exposure of the interface to solutions containing non-ionic polymers.

Yet other embodiments of the invention are directed to a modified liquid crystal comprising a liquid crystal layer and a polyelectrolyte multilayer film deposited on the liquid crystal layer. The polyelectrolyte multilayer film is deposited directly on the liquid crystal layer or, alternatively, a lipid having a charged head group is present at the interface that facilitates formation of the PEM film. In preferred embodiments, the polyelectrolyte multilayer film includes an excipient capable of interacting with an analyte present in an aqueous phase contacted with the polyelectrolyte multilayer film, the interacting causing a change in the orientational ordering of the liquid crystal layer. In particularly preferred embodiments, the excipient is a ligand or a receptor capable of selectively-binding the analyte. Alternatively, the excipient is a molecule capable of undergoing a chemical reaction in the presence of the analyte. In another embodiment, the excipient is an enzyme substrate capable of being transformed by an enzymatic analyte. Alternatively, in yet another embodiment, the excipient is an enzyme that can catalyze the transformation of an analyte. As well, the liquid crystal may be in the form of a droplet such that the polyelectrolyte multilayer film is deposited on the droplet.

In yet another embodiment, the invention provides a method of detecting an analyte contained in an aqueous solution. Such a method includes steps of: (a) contacting an aqueous solution containing an analyte with a polyelectrolyte multilayer film deposited on a liquid crystal; and (b) determining whether a change in orientational ordering of the liquid crystal occurs as the aqueous solution containing the analyte is contacted with the polyelectrolyte multilayer film deposited on the liquid crystal. The presence of the analyte in the aqueous solution is indicated by the change in the orientational ordering of the liquid crystal.

In preferred detection methods, the polyelectrolyte multilayer film includes an excipient capable of interacting with an analyte present in the aqueous phase contacted with the polyelectrolyte multilayer film, the interacting causing a change in the orientation of the liquid crystal layer. In particularly preferred embodiments, the excipient is a ligand or a receptor or an enzyme capable of selectively-binding or transforming the analyte. Alternatively, the excipient is a molecule capable of undergoing a chemical reaction in the presence of the analyte. In another embodiment, the excipient is an enzyme substrate capable of being transformed by an enzymatic analyte. Alternatively, in yet another embodiment, the excipient is an enzyme that can catalyze the transformation of an analyte.

In yet a further embodiment, the invention encompasses a liquid crystal device, comprising: (a) a container; (b) a liquid crystal disposed within said container; and (c) a polyelectrolyte multilayer film deposited on a surface of the liquid crystal.

In another embodiment, the invention encompasses a method for providing an unsupported PEM film, the method including steps of (a) providing a liquid-liquid interface between immiscible first and second liquids; and (b) sequentially-depositing layers of cationic and anionic polyelectrolytes at the liquid-liquid interface whereby a polyelectrolyte multilayer film is provided at the liquid-liquid interface; and (c) removing the first and second liquids to provide an unsupported polyelectrolyte multilayer film. In certain embodiments, one of the liquids is provided in the form of a droplet and the unsupported polyelectrolyte multilayer film formed by the method is in the general shape of a hollow sphere or capsule. A particularly preferred method includes steps of: (a) preparing an aqueous-liquid crystal interface between an aqueous phase and a liquid crystal phase; (b) depositing alternating layers of cationic and anionic polyelectrolytes at the aqueous-liquid crystal interface whereby a polyelectrolyte multilayer film is provided at the aqueous-liquid crystal interface; and (c) removing the aqueous phase and the liquid crystal phase to provide an unsupported polyelectrolyte multilayer film.

Other objects, features and advantages of the present invention will become apparent after review of the specification, claims and drawings.

DETAILED DESCRIPTION OF THE INVENTION

I. In General

Figure 1:
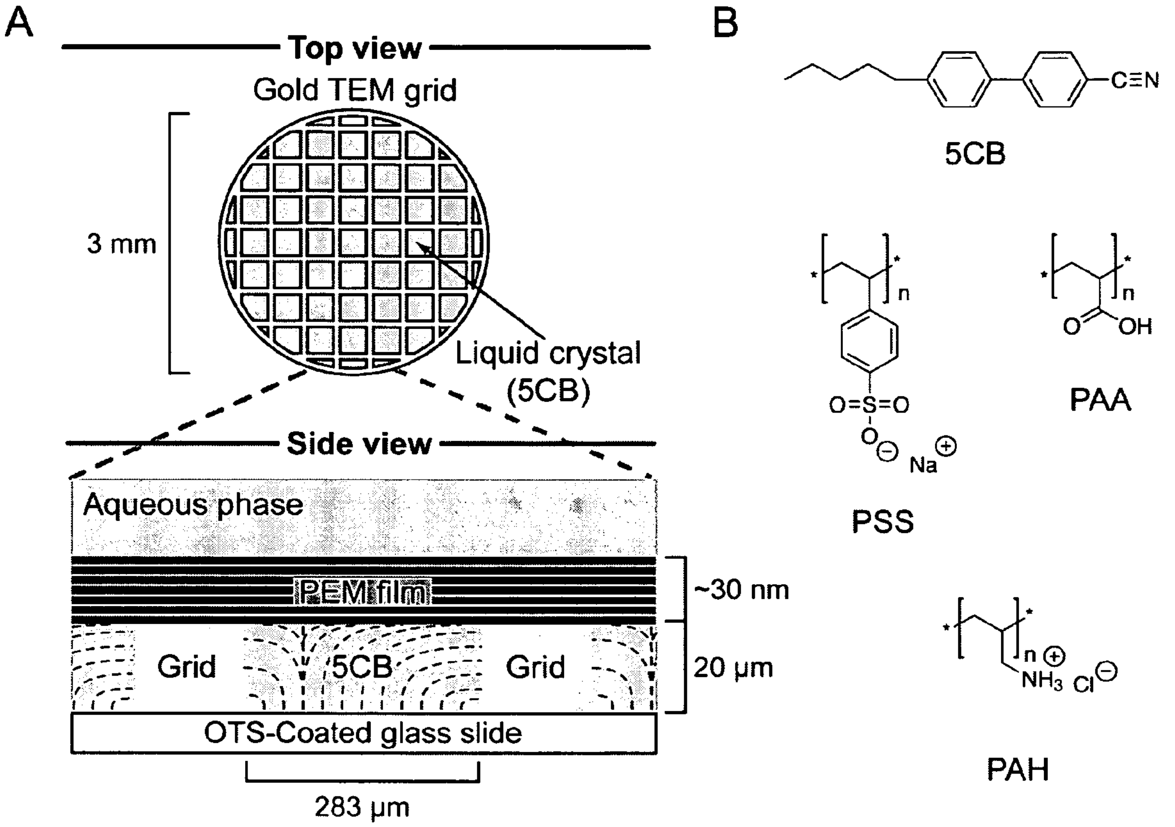
FIG. 1 A) Schematic illustration of the geometry for producing planar interfaces between aqueous phases and immiscible thermotropic liquid crystals. An example of the director profile in the liquid crystal film for planar anchoring is also shown. The thicknesses of the slide, grid, and PEM film are not to scale. B) Structures of the liquid crystal 5CB and polyelectrolytes PSS, PAA, and PAH, referred to herein.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, the term "polyelectrolyte" shall mean a polymeric substance, either natural (e.g., protein, nucleic acid, or carbohydrate) or synthetic (e.g., poly(allylamine hydrochloride or poly(acrylic acid)), containing ionic or partially charged constituents being either cationic or anionic.

The term "liquid crystal", as used herein, refers to an organic composition in an intermediate or mesomorphic state between solid and liquid. Suitable liquid crystals for use in the present invention include, but are not limited to, thermotropic, lyotropic, chromonic, smectic, nematic, ferroelectric and cholesteric liquid crystals. The liquid crystals used in the scope of the invention may also incorporate nanoparticles such as, e.g., metallic nanoparticles.

The term "polyelectrolyte multilayer films" or "PEM films", as used herein, shall refer to films having at least one "bilayer" of deposited polyanion and polycation. The term "bilayer", as used herein, shall refer to the accumulated layers of material deposited on a surface as a result of having passed through at least one complete cycle of the general methodologies described below and schematically shown in, e.g., FIG. 2. Use of the term "PEM film" or "bilayer" herein is not intended to place a restriction on the types of structures that are formed as a result of having passed through at least one complete cycle of the general methodologies described below and schematically shown in, e.g., FIG. 2 and described in this disclosure. The term "bilayer" shall refer to the sequential exposure of the interface to separate solutions of two polyelectrolytes. It is widely understood by those skilled in the art that the sequential exposure of an interface to polyelectrolytes of opposite charge can lead to a range of interfacial structures and that in some cases there is substantial mixing of the PEM with the polyelectrolyte in solution to which the PEM is exposed. In some cases, the growth of the PEM occurs linearly with the number of cycles of exposure, in other cases so-called exponential growth regimes are observed. Preferred embodiments utilize films having at least two bilayers of polyanion and polycation although specific applications will dictate the optimum number of bilayers to be determined by no more than routine experimentation.

The following abbreviations are used throughout the present disclosure:

LbL, layer-by-layer; PEM, polyelectrolyte multilayer; PSS, poly(sodium-4-styrenesulfonate); PAH, poly(allylamine hydrochloride); PAA, poly(acrylic acid); FITC-PAH, fluorescein isothiocyanate-labeled poly(allylamine hydrochloride; 5CB, 4'-pentyl-4-cyanobiphenyl; DLPS, 1,2-Dilauroyl-sn-glycero-3-[phospho-L-serine]; DLEPC, 1,2-dilauroyl-sn-glycero-3-ethylphosphocholine; SDS, sodium dodecyl sulfate, DTAB, dodecyltrimethylammonium bromide.

II. The Invention

The preparation of PEMs at liquid-liquid interfaces according to the invention involves (1) preparing or providing an interface between immiscible first and second liquid phases, and (2) depositing alternating layers of polycationic and polyanionic polymers at the liquid-liquid interface. Methods of PEM formation at liquid-liquid interfaces will now be described by reference to an aqueous-liquid crystal example. However, it should be realized that the methods according to the invention are not to be limited to any one particular liquid-liquid combination (e.g., aqueous-liquid crystal) but are applicable to PEM formation at wide variety of liquid-liquid interfaces formed between immiscible first and second liquids. Referring now to FIG. 1A, a suitable interface between an aqueous phase and a liquid crystal is depicted where liquid crystal is hosted in the pores of a gold transmission electron microscope (TEM) grid sitting atop a glass substrate. The present example employs an approximately planar interface between a representative liquid crystal, in this case, the nematic liquid crystal 4'-pentyl-4-cyanobiphenyl (5CB), and an aqueous solution. This assembly is prepared as follows: Glass slides are treated with octadecyltrichlorosilane (OTS). Gold specimen grids are placed onto the surface of glass, and liquid crystal was dispensed onto each grid and the excess liquid crystal removed with a syringe to produce an approximately planar surface. This geometry permits easy observation and interpretation of the orientations of the liquid crystals at the aqueous-5CB interface and enables the sequential contact of aqueous solutions containing polyelectrolytes of opposite charge (e.g., PSS, PAA and PAH; respective structures for these compounds shown in FIG. 1B), leading to the formation of PEM films.

The formation of PEMs at aqueous-liquid crystal interfaces then proceeds by one of two alternative methods. As one of skill in the art will appreciate after review of this disclosure, the two alternative approaches are certainly applicable to PEM formation at other liquid-liquid interfaces including, for example, aqueous-oil interfaces. In a first exemplary method depicted at the left hand side of FIG. 2, PEMs are formed directly at the aqueous-liquid crystal interface by exchanging the water phase with a solution of polyanion, in this case, poly(sodium-4-styrenesulfonate) (PSS). The PSS solution is exchanged with water after a suitable period of time (e.g., 15 minutes), and the water is exchanged several times to rinse away any PSS not strongly adsorbed to the water-liquid crystal interface. Then a solution of polycation, in this case, poly(allylamine hydrochloride (PAH), is introduced and incubated for a period of time (e.g., 15 minutes). After rinsing with water, the process is repeated to produce PEMs possessing a pre-selected number of polyanion/polycation bilayers (e.g., ten PSS/PAH bilayers). In support of broad applicability beyond the aqueous-liquid crystal context, additional examples of PEM formation at liquid-liquid interfaces using the methods described and claimed herein are provided in the examples section below (see, e.g., Example 7 which teaches PEM formation at an aqueous-isotropic oil interface).

The polyelectrolytes that can be used in the present invention include, but are not limited to, synthetic, linear polyelectrolytes; dendrimers; charged biomolecules such as polynucleotides, proteins and polysaccharides; or polyvalent small molecular weight organic compounds. Exemplary polycations and polyanions useful in the formation of PEM films according to the invention include, but are not limited to the following polymers to which ionic groups are covalently attached: polystyrenes, polyamines, polyesters, non-biodegradable polyurethanes, polyureas, poly(ethylene vinyl acetate), polypropylene, polymethacrylate, polyethylene, polycarbonates, and poly(ethylene oxide)s. Particularly preferred polymers for use in the invention include: poly(styrene sulfonate) (SPS), poly(acrylic acid) (PAA), linear poly(ethylene imine) (LPEI), poly(diallyldimethyl ammonium chloride) (PDAC), poly(allylamine hydrochloride) (PAH); and poly(sodium-4-styrenesulfonate) (PSS). Degradable polymers such as polylactic acid and polyglycolic acid may also be used in the present invention. The polyelectrolytes can also include naturally occurring components of the extracellular matrix of cells (e.g., laminin and collagens) or synthetic polymers that incorporate peptides found in these naturally occurring polypeptides. The polyelectrolytes can also be peptide or synthetic substrates for enzymes such as proteinases and proteases. The polyelectrolytes that can be used in the present invention include organic and inorganic nanoparticles that have been widely demonstrated to be incorporated into PEMs formed at the surfaces of solids. For example, citrate stabilized gold nanoparticles are polyelectrolytic materials that can be incorporated into PEMs. Other examples include carbon nanotubes and other inorganic nanostructures chemically treated by using methods well known to those skilled in the art (e.g., treatment with oleum) to charge the surface of the nanostructures. It has also been demonstrated that multilayer films of non-ionic polymers can be formed by the layer-by-layer methods using procedured identical to those used to form polyelectrolyte films. Thus the methods described herein include formation of multilayer films from non-ionic polymers.

Figure 2:
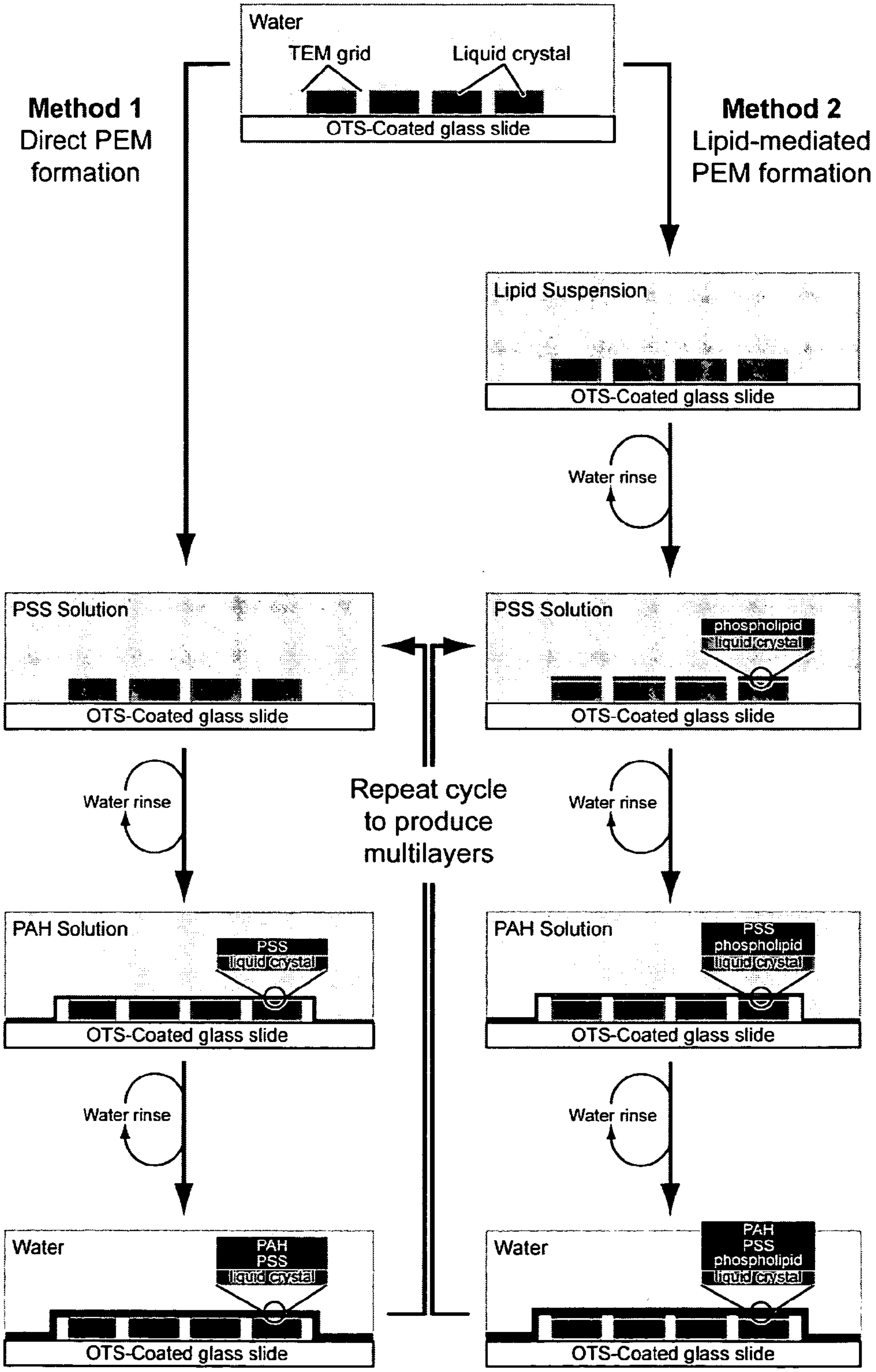
FIG. 2. Procedure for preparation of PEMs at an aqueous-LC interface. Method 1 (left) yields PEMs directly on the liquid crystal, while Method 2 (right) incorporates a monolayer of charged lipid between the liquid crystal and the PEM thereby facilitating deposition of polyelectrolytes that do not partition to the aqueous-liquid crystal interface.

In an alternative method illustrated at the right hand side of FIG. 2, formation of PEMs is carried out on lipid-laden aqueous-liquid crystal interfaces. The aqueous-liquid crystal interface can first be seeded with a lipid with a charged headgroup. The water phase is exchanged with a dispersion or solution of charged lipid, and the lipids are allowed to adsorb to the aqueous-liquid crystal interface for a period of time (e.g., 30 minutes). The lipid dispersion or lipid solution is exchanged with water and the system rinsed before introducing a solution of polyelectrolyte that has the opposite charge of the lipid layer. PEM formation then proceeds as described for the first method described in the preceding paragraph.

Various liquid crystals may be employed in liquid crystal-related applications of the present invention. Examples of suitable liquid crystals, include, but are not limited to, 4-cyano-4'-pentylbiphenyl (5 CB), 7 CB, and 8 CB. A large listing of suitable liquid crystals is presented in "Handbook of Liquid Crystal Research" by Peter J. Collings and Jay S. Patel, Oxford University Press, 1997, ISBN 0-19-508442-X. Polymeric liquid crystals are also suitable for use in the device and methods of the present invention. Because the devices and methods of the present invention include contacting the liquid crystal with aqueous solutions, preferred liquid crystals employed in the invention should be insoluble in water or have very limited solubility in water. Additionally, preferred liquid crystals employed in the invention should not react with water. In one embodiment of the present invention, the liquid crystal deposited in the holding compartment of the substrate (in a grid cavity or in the depression in a support with a surface defining a depression) is 4-cyano-4'-pentylbipheny-1 (5 CB). Although various types of liquid crystal may be employed, nematic and thermotropic liquid crystals are preferred. However, smectic liquid crystals formed from 8 CB are also suitable for use in the present invention. Suitable liquid crystals further include smectic C, smectic C*, blue phases, cholesteric phases, smectic A, and polymeric liquid crystals. In other embodiments of the invention, the liquid crystal is a lyotropic liquid crystal formed in the aqueous phase and an oil is used that is immiscible with the lyotropic liquid crystal. The lyotropic liquid crystal may be formed from nanoparticles.

It can be appreciated that a liquid crystal may be placed in one or more grid(s) or depression(s) of a suitable substrate using various techniques. For example, a liquid crystal may be deposited in a grid or well using a microliter syringe. As described above and in the Examples, a microliter capillary tube may then be used to remove excess liquid crystal from the substrate surface. In one embodiment, a liquid crystal in a holding compartment of a substrate is heated into its isotropic phase at a temperature of about 50° C. and is then plunged into water at a temperature ranging from about 20° C. to 25° C. This methodology has been found effective at removing air bubbles and excess liquid crystal and for producing suitable liquid crystal devices ready for adsorption of a selected receptor molecule. As noted above, the liquid crystal is typically deposited into the grid or depression using a microliter syringe. The liquid crystal may also be deposited into the grid or depressions by first dissolving the liquid crystal in a volatile organic solvent such as hexane, pentane, heptane, methylene chloride, or chloroform, depositing an appropriate amount of the dissolved liquid crystal on the grid or depression, and allowing the solvent to evaporate leaving the liquid crystal in the grid. The liquid crystal may also be deposited in the grids or depressions using microfluidic channels placed over the patterned surface or grid. A liquid crystal may then be injected into the microfluidic channels and drawn into the grids or depressions by capillary action or pressure-driven flow. In other alternative embodiments, the liquid crystal is deposited into the grid by using inkjet printing (drop-on-demand) technology.

In general, the invention is directed to liquid-liquid interfaces functionalized by the presence of a PEM film. This functionalization is particularly useful in the context of aqueous-liquid crystal interfaces where it is understood that liquid crystals near interfaces are highly sensitive to the nature of the interactions between the mesogens forming the liquid crystal and a confining interface. Accordingly, a PEM film may, depending on interactions with molecules present in the aqueous phase, cause changes in the orientational ordering of the liquid crystal. Example 5 below illustrates an example of a PEM film selectively mediating interactions between two differing analytes present in the aqueous phase and a liquid crystal. Specifically, Example 5 demonstrates how a liquid crystal functionalized according to the invention is caused to discern between the two surfactants, sodium dodecyl sulfate (SDS) and dodecyltrimethylammonium bromide (DTAB), respectively, in aqueous solution. In effect, a PEM film provided at an aqueous-liquid crystal interface may tailor the selectivity of the liquid crystal in regard to the liquid crystals response to particular analytes of interest.

As is known to those skilled in the art, changes in optical properties of the liquid crystal can be quantified by using optical instrumentation such as, but not limited to, plate readers, cameras, scanners, photomultiplier tubes. Because the dielectric properties of liquid crystals also change with orientational order, measurements of electrical properties of liquid crystals can also be used to report changes in the interactions of molecules with liquid crystals. In some embodiments of the present invention, the optical and electrical measurements lead to determination of the anchoring energy of the liquid crystal at the PEM-decorated interface. In one embodiment, the torque-balance method is used to determine the anchoring energy.

In certain liquid crystal-related embodiments, the invention is directed to PEM films that include one or more excipients so as to, in combination with the PEM film, functionalize a liquid-liquid interface. Accordingly, excipients present in a PEM film may, depending on interactions with each other, the PEM film, and/or molecules present in the aqueous phase, cause changes in the orientation of the liquid crystal.

For example, various receptor species may be combined with the PEM film and, if an aqueous solution includes a sufficient amount of a compound that interacts with the receptor species, a change in the orientation of the liquid crystal will occur indicating the interaction (binding and/or chemical reaction) between the receptor species and the compound. Typically, the liquid crystal is viewed through polarized light to determine whether the orientation has been altered. In one embodiment, a polarized light microscope is used and may further be used in conjunction with cross polarizers.

Examples of suitable receptor species to be combined with a PEM film include, but are not limited to peptides and proteins, including integral membrane proteins such as glycoproteins, cell signaling proteins such as G proteins, growth factor receptors, ion channel proteins, antibodies, proteoglycans, and integrins. As well, molecules such as hormones (e.g. estrogen, testosterone, glucagons, and epinephrine), hormone receptor proteins, growth factors, insulin, biotin, sugars (e.g. glucose, lactose), DNA, RNA, collagen, pharmaceuticals, enzyme inhibitors, peptides, polypeptides, nucleotides, oligonucleotides, antibodies, immunoglobulins, chelating agents, and metal ions (collectively, "ligands") may also be contained within the PEM film. Those skilled in the art will recognize that various other molecular species may be used in accordance with the present invention. For example, enzymes or substrates for enzymes can be incorporated into PEM films.

As directed herein, aqueous solutions containing compounds may be contacted with a PEM film including an excipient on a liquid crystal to detect interactions or chemical reactions between the compound and the excipient. In this manner, the present invention allows one to detect interactions (binding and/or chemical reaction) of known analytes with a given excipient or may be used to detect or identify a given analyte in an aqueous solution. Various analytes may be determined in accordance with the present invention. A liquid crystal device prepared using an appropriate PEM in combination with a receptor or ligand species may be used to detect eukaryotic and prokaryotic organisms, bacteria, viruses, DNA, RNA, proteins, enzymes, ions, and cells in an aqueous solution that is circulated or passed over or contacted with the functionalized PEM film atop the liquid crystal. The role of the excipient and analyte may be reversed by changing which species is hosted within the PEM layer at the liquid crystal-aqueous interface. Examples of such interactions are biotin and avidin, streptavidin, and antibiotin-IgG; growth factors and growth factor receptors; hormones and hormone receptors; enzymes and enzyme inhibitors, substrates, and initiators; antibodies and antigens; integrins and components of the extracellular matrix; cell signaling proteins as part of a cascade; and ion channel proteins and ions and activating ligands. Generally, analyte concentrations in the aqueous solutions may range from 1 fM to 1 M with the desirable concentration depending on the nature of the interaction between the analyte and the receptor. For biological analytes, the pH of aqueous solutions should typically range from 6 to 9.

In one embodiment, the invention provides a method for determining a change in the oxidation state of a molecule contained within a PEM film overlaying a liquid crystal. In such embodiments, the molecule includes a group such as, but not limited to, a ferrocene group that may be oxidized or reduced upon contact with an oxidizing agent, a reducing agent, an applied oxidizing potential, or an applied reducing potential. In the method, a liquid crystal device immersed in an aqueous solution is contacted with an oxidizing agent, a reducing agent, an applied oxidizing potential, or an applied reducing potential. In the liquid crystal device of such methods, the molecule is contained within a PEM film deposited on the top surface of a liquid crystal that is located in the holding compartment of a substrate as described above. A change in the orientation of the liquid crystal upon contacting the liquid crystal device with the oxidizing agent, the reducing agent, the applied oxidizing potential, or the applied reducing potential indicates that the oxidation state of the molecule has changed. Examples of groups that may be oxidized or reduced on the receptor molecule include, but are not limited to, ferrocene, quinone, metal tri-nitriloactetic acid complexes, ferricyanide, viologens, metal porphyrins, alcohols, aldehydes, organosulfur compounds, anthracene, azobenzene, benzophenone, nitrobenzene, $Ru(bpy)_3^{n+}$, tetracyanoquinodimethane (TCNQ), tetrathiafulvalene, and other biological redox-active species such as but not limited to neurotransmitters. One group of suitable molecules with groups that may be oxidized or reduced includes (ferrocenylalkyl)trialkyl-ammonium halides such as (ferrocenylalkyl) trimethylammonium chlorides and bromides such as 11-(ferrocenylundecyl)trialkylammonium bromide. The aqueous solution in which the liquid crystal device is immersed may also include surfactants such as cationic surfactants, anionic surfactants, and/or zwitterionic surfactants. Examples include ferrocenyl surfactants; alkyltrimethylammonium halides; alkyl sulfates; phospholipids such as dilaurylphosphatidyl choline, dipalmitoylphosphatidyl choline, dilaurylphosphatidyl ethanolamine, dipalmitoylphosphatidyl ethanolamine, and combinations of these; and polymeric surfactants, such as hydrophobically modified ethylhydroxyethyl cellulose (HM-EHEC). Quaternary ammonium compounds suitable for use as surfactants include, but are not limited to, CTAB and DTAB. Typically, the aqueous solution also includes a salt such as, but not limited to, $Li_2SO_4$. Other buffering agents and salts may be included in the aqueous solutions such as, but not limited to, sodium halides, potassium halides, sodium sulfate, potassium sulfate, sodium phosphate, potassium phosphate, tris, HEPES, and MOPS.

The present methodology may be adapted to a variety of liquid crystal device designs. For example, the present methodology may be employed to modify a variety of liquid crystal devices, including those described in U.S. Published Patent Application 2003/0194753 A1 to Abbott et al., which is incorporated herein by reference. In general, liquid crystal devices useful in the present invention will include a container having an inlet and an outlet with the liquid crystal housed in the container on a suitable substrate. For example, the device may include a glass slide on which a grid is positioned that is disposed inside a container. The container includes an inlet and an outlet through which a sample may be introduced and removed from container. Inlet and outlet may be configured to project out the sides of container or alternatively may simply be holes defined by side walls. Those skilled in the art will recognize that various other configurations are possible and may be used.

Quantitative determination of kinetic parameters from the appearance of the liquid crystal may be accomplished by plotting a measure of the optical texture (such as the average brightness (grayscale or an RGB channel), standard deviation of any measure of brightness, anchoring energy, or a Fourier transform of the image) versus time. Electrical measurements, as described above, can also be performed and quantified. The data may then be analyzed by fitting the data with a model of the kinetic behavior for the given interaction (e.g. a surface reaction analogue to the Michaelis-Menton equation for enzyme kinetics).

Because the devices of the present invention may be used to detect the presence of compounds in flowing streams, the devices may be used to continuously monitor the presence of a compound that interacts with the PEM film or PEM film/excipient combination on the surface of a liquid crystal. Additionally, the devices of the present invention may be used to monitor water quality.

In certain embodiments, the formation of PEMs at liquid-liquid interfaces is useful to mechanically stabilize an interface or to immobilize agents such as catalysts of reactions at the interface. For example, if an enzyme is incorporated into a PEM at a liquid-liquid interface then the substrates and products of the enzymatic reaction could be delivered to and from the enzyme via either side of the PEM at the liquid-liquid interface. In addition, systems containing multiple enzymes could be hosted within PEMs formed at liquid-liquid interfaces. The capacity of the PEM to host the enzyme could be substantially greater than is possible when enzymes adsorb directly at liquid-liquid interfaces. In addition, the microenvironment of the enzyme can be controlled by the structure of the PEM, thus maximizing the activity and stability of the enzyme.

In other embodiments, PEMs formed at liquid-liquid interfaces are used to prevent the adsorption of biomolecules and other molecules at liquid-liquid interfaces, thus preventing the fouling of the interface.

PEMs formed at liquid-liquid interfaces are also envisioned to change the rheological properties of the interfaces, which finds use in stabilizing emulsions and other dispersed liquid phases used in, for example, cosmetic formulations and drug delivery. PEMs formed at interfaces of emulsion droplets can provide means of encapsulation for, for example, protection of the encapsulant from the environment or controlled release of the encapsulant.

The methods of the present invention may also be used to create three-dimensional microstructures consisting of unsupported PEM films. The formation of PEMs at liquid-liquid interfaces certainly enables a general and facile route to the fabrication of free standing PEM structures when the liquids are chosen to be easily removed from the PEM. For example, the PEM film may be deposited at a liquid-liquid interface which is then removed by dissolving one or more liquid phases, drying one or more liquid layers, or applying other suitable means to leave an unsupported PEM film. Example 4 below describes the fabrication of unsupported PEM films by drying an aqueous phase and then dissolving a liquid crystal phase to leave the PEM film, previously deposited there between, in a free-standing microstructure. It will be appreciated that more complex microstructures could be created based on these simple principles (e.g., by depositing PEMs with different electrostatic characters in different liquid-liquid regions and/or by iterative additions of subsequent structures above the deposited polymer).

The formation of unsupported PEM films prepared as described above provides a general and facile method for the fabrication of nano-, micro- and milli- and larger scale structures. By incorporation of various polyelectrolytes into the PEM, it is possible to make drug delivery nano or micro devices that are transported to a tumor or wound and release active ingredients that destroy the tumor or heal the wound. Many other possible applications for such unsupported PEM films exist, including, but not limited to, sensors that are formed from asymmetric PEM structures and that change shape upon encountering a targeted analyte. Unsupported PEM structures could also be used for chemomechanical transduction and other types of energy exchange where the reaction of a chemical species with one surface of the PEM leads to a mechanical deformation of the PEM against a resisting force. Other applications are evident to those skilled in the art of fabricating unsupported nano- and micro-structures.

The inventors have previously shown that it is possible to prepare, e.g., layer-by-layer (LbL) films on an approximately planar interface between the nematic LC 4'-pentyl-4-cyanobiphenyl (5CB) hosted in a gold grid, and an aqueous phase (water). The LbL films preserved the planar anchoring of 5CB in water. Furthermore, the multilayer films were observed to mediate the interactions between solutes dissolved in the aqueous phase and the LC. One attractive feature of using LbL assembly to modify the surface properties of LCs is the flexibility of the approach: different materials can be assembled, including polymers, proteins, DNA, multivalent ions, and nanoparticles. The technique can be also transferred to three-dimensional substrates, such as colloidal particles, biomolecule crystals, macroporous membranes, and porous beads. Recently, three-layered polymer membranes (consisting of lecithin, chitosan and pectin) were deposited on oil-in-water emulsions of tuna or corn oil. These polymers were deposited without intermediate washing steps and significant droplet aggregation was observed.

Accordingly, emulsions formed from LCs are useful for creation of LC-based sensors because they have a much higher surface area than LCs formed at planar interfaces, they are mobile, and frustrated states assumed by LCs within droplets provide an additional opportunity to tune the response of LCs to interfacial events. Previous studies on LC emulsion droplets have shown their usefulness for studying a variety of phenomena, including the rotational motion of particles, the effect of hydrodynamic flows, and the effect of electric fields. Such emulsions have been prepared by methods including photo-polymerization, dispersion polymerization, shearing droplets and subsequent crystallization fractionation, ultrasonication and droplet break-off in a co-flowing stream.

In an example below, the inventors illustrate how stable nematic LC emulsions are formed by sonication. In this particular exemplary embodiment, layer-by-layer growth of multilayers of PAH and PSS on micrometer-sized 5CB-PSS and 5CB-DLEPC emulsion droplets was confirmed with ζ-potential measurements, flow cytometry, and fluorescence microscopy. The LC in the 5CB-PSS emulsion droplets assumed a bipolar configuration while the LC in the 5CB-DLEPC emulsion droplets adopted a radial configuration, and these configurations were preserved after multilayer assembly. In addition, the multilayers were used to influence the interaction of analyte with the LC core. When the 5CB cores of the multilayer-coated emulsion droplets were dissolved with ethanol, hollow capsules were formed. The exemplary results demonstrate that LbL assembly can be applied to the mobile interfaces between LC droplets and aqueous phases, which represent an important development in the preparation of chemically-tailored interfaces for use in micrometer-sized biological and chemical sensors. In addition, this approach is applicable to other oils, allowing a versatile route to produce hollow polymeric capsules. Such a development offers considerable advantages over solid templates.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

The following materials and methodologies were utilized in the examples discussed in greater detail below.

Materials. Poly(sodium-4-styrenesulfonate) (PSS, $M_w$, 70 kDa) and poly(allylamine hydrochloride) (PAH, $M_w$, 70 kDa) were purchased from Sigma-Aldrich and used without further purification. PAA was purchased from Polysciences. Fluorescein isothiocyanate-labeled PAH (FITC-PAH, $M_w$, 70 kDa) was prepared as described by Caruso and coworkers. The nematic liquid crystal 4'-pentyl-4-cyanobiphenyl (5CB) was purchased from EMD Chemicals (Hawthorne, N.Y.) and used without further purification. Gold specimen grids (bars 20 μm thick and 55 μm wide, spaced 283 μm apart) were obtained from Electron Microscopy Sciences (Fort Washington, Pa.) and cleaned sequentially in ethanol, methanol, and methylene chloride. The phospholipids 1,2-Dilauroyl-sn-glycero-3-[phospho-L-serine] (DLPS) and 1,2-dilauroyl-sn-glycero-3-ethylphosphocholine (DLEPC) were purchased from Avanti Polar Lipids (Alabaster, Ala.). Sodium dodecylsulfate (SDS) was purchased from Sigma-Aldrich. SDS was purified by recrystallization from ethanol. Deionization of a distilled water source was performed with a Milli-Q system (Millipore, Bedford, Mass.) to give water with a resistivity of 18.2 MΩ·cm. Glass microscope slides were Fisher's Finest Premium Grade obtained from Fisher Scientific (Pittsburgh, Pa.). Octadecyltrichlorosilane (OTS) was obtained from Fisher Scientific. Sylgard 182 elastomer and curing agent (PDMS) was obtained from Dow Corning Corp. (Midland, Mich.). 2 Ton Clear epoxy resin and hardener was obtained from ITW Devcon (Danvers, Mass.).

Preparation of optical cells. A detailed description of the methods used to prepare and examine the liquid crystal hosted within optical cells can be found in Brake et al. *Langmuir* 2002, 16, 6101. Briefly, glass microscope slides were cleaned according to published procedures (Skaife et al. *Chem. Mater.* 1999, 11, 612) and coated with octadecyltrichlorosilane (OTS). The quality of the OTS layer was assessed by checking the alignment of 5CB confined between two OTS-treated glass slides. Any surface not causing homeotropic anchoring of 5CB was discarded. A small square of OTS-coated glass (ca. 5 mm×5 mm) was fixed to the bottom of each well of an 8-well chamber slide (Nalge Nunc International, Rochester, N.Y.) with epoxy and cured overnight at 60° C. The wells were rinsed several times with ethanol to remove uncured monomer and subsequently dried. Gold specimen grids that were cleaned sequentially in methylene chloride, ethanol, and methanol were placed onto the surface of the OTS-treated glass slides, one per well. Approximately 1 μL of 5CB was dispensed onto each grid and the excess liquid crystal was removed with a syringe.

Preparation of phospholipid solutions. The appropriate amount of chloroform solutions of the phospholipids DLPS or DLEPC (10 mg/mL) were dispensed into glass tubes and dried under a stream of nitrogen. The tubes were then left to dry under vacuum overnight and stored in a −20° C. freezer until needed. The lipids were reconstituted to 100 micromolar in water, hydrated overnight at room temperature, and sonicated for 30 min in a bath sonicator. Upon reconstitution the lipid solutions were clear and were used without filtering. The dried lipids were resuspended and used within one month of drying.

Liposome preparation. Chloroform solutions of pure DLPS or DLEPC were dispensed in a glass tube and dried under a low flow of $N_2$ to form a thin lipid film. Residual solvent was removed under vacuum at 50° C. for several hours. The resulting lipid film was hydrated overnight at room temperature (above the lipid transition temperature) with an appropriate volume of water to yield a final lipid concentration of 100 μM. The lipid solutions appeared clear after this step, suggesting that both DLPS and DLEPC either dissolved or formed micellar aggregates in solution. Nevertheless, the lipid suspensions were sonicated for 30 min in a bath sonicator at room temperature to produce small unilamellar liposomes. Upon reconstitution the lipid solutions were clear and were used without filtering.

LbL Deposition at aqueous-liquid crystal interface. PSS, PAH and PAA solutions were of concentration 1 mg/mL in 0.1 M or 0.5 M NaCl. FITC-PAH solutions were of concentration 0.2 mg/mL in 0.25 M or 0.5 M NaCl. PAH and PAA solutions used to form PAH/PAA multilayers were adjusted with HCl to pH 7.0; the pH was not adjusted for other solutions. For adsorption of each polyelectrolyte at the aqueous-liquid crystal interface, 1 mL of polyelectrolyte solution was flowed through the flow cell and incubated for 10 min (0.1 M NaCl) or 15 min (0.5 M NaCl). Three 1 mL aliquots of water were then rinsed through with 1 min incubation each to remove free polyelectrolyte from the cell. In the absence of lipid seeding, PSS/PAH multilayers were started with PSS. A PSS layer followed DLEPC seeding of aqueous-liquid crystal interfaces and PAH followed DLPS-seeding. FITC-PAH layers were followed by five 1 mL water rinses to remove any free fluorescent molecules.

Polarized microscopy of PEMs at aqueous-liquid crystal interface. The orientation 5CB within each optical cell was examined with plane-polarized light in transmission mode on an IX-71 inverted microscope with crossed polarizers. The source light intensity levels were constant for all images of the same magnification. Homeotropic alignments of the liquid crystal were determined by observing the absence of transmitted light regardless of rotation of the sample. Images were taken with a QImaging MicroPublisher 3.3 RTV color camera on autoexposure (unless noted) and controlled via ImagePro Express software.

Fluorescent microscopy of PEMs at aqueous-liquid crystal interface. PEMs were prepared at the aqueous-liquid crystal interface as described above and then imaged with an Olympus IX-71 inverted microscope using a fluorescence filter cube with an excitation filter and emission filter. Images were taken with a QImaging MicroPublisher 3.3 RTV color camera controlled via ImagePro Express software. Unless noted, the exposure times for 4× and 10× images were 2 s and 500 ms, respectively. The fluorescent images were taken with the liquid crystal/OTS glass interface toward the objective.

EXAMPLE 1

Procedure for Preparation of PEMs at the Aqueous-LC Interface

In this example, the direct formation of a PEM film at an aqueous-liquid crystal interface is described. PEM films were formed directly at an aqueous-5CB interface by initially contacting the surface of the 5CB for 15 minutes with a solution of poly(styrene-4-sulfonate) (PSS, 1 mg/mL in 0.5 M NaCl), which has been shown to partition onto hydrophobic interfaces, and alternately exposing the interface to a solution of poly(allyl amine hydrochloride) (PAH, 1 mg/mL in 0.5 M NaCl). These steps were repeated ten times. Initial experiments used the standard method of dipping the substrate (in our case, 5CB hosted in a TEM grid on a glass slide) into each solution. However, this process sometimes (but not always) displaced the 5CB from the grid upon its passage through the air-water meniscus. The inventors found that a more reliable method was to place the grid containing 5CB at the bottom of a small well and exchange solutions in such a way that the meniscus never fell below the interface of the 5CB.

To verify that a PEM film formed at the aqueous-5CB interface, one or more layers of fluorescently-labeled PAH (FITC-PAH) were incorporated into the film. Fluorescence imaging showed the incorporation of FITC-PAH into the film at the aqueous-5CB interface (data not shown). To quantify the build-up of the PEM film, the inventors deposited three bilayers of PSS/PAH directly at the aqueous-5CB interface followed by seven bilayers of PSS/FITC-PAH. The fluorescence intensity of the regions within the grid squares (i.e., corresponding to regions of PEM film deposited on 5CB) increased linearly with the number of FITC-PAH layers (FIG. 3A). These results confirm the formation of PEM films directly at the aqueous-5CB interface.

EXAMPLE 2

Procedure for Preparation of PEMs at the Aqueous-LC Interface

This example describes an alternative approach leading to formation of PEM films on the aqueous-5CB interface by the seeding of the aqueous-5CB interface with the anionic phospholipid 1,2-dilauroyl-sn-glycero-3-[phospho-L-serine] (DLPS) or the cationic phospholipid 1,2-dilauroyl-sn-glycero-3-ethylphosphocholine (DLEPC) prior to introducing the initial polyelectrolyte. Phospholipids in the form of an aqueous suspension of small unilamellar vesicles have previously been shown to spontaneously adsorb to hydrophobic interfaces, including liquid crystals. After forming DLPS or DLEPC monolayers at the aqueous-5CB interface by incubating the interface in a solution of small unilamellar vesicles (100 micromolar lipid in water), the inventors exchanged the lipid solution for a lipid-free solution and subsequently introduced polyelectrolyte solutions (1 mg/mL in 0.5 M NaCl) in order to form PEM films. For DLEPC-laden interfaces, which are cationic in nature, the inventors first incubated the interface in a poly(acrylic acid) (PAA) solution for 15 minutes, and alternated with PAH solutions for the same amount of time. For anionic DLPS-laden interfaces, the inventors started with PAH and alternated with PAA. The process was repeated ten times and used a FITC-labeled PAH as the final PAH layer in both cases. Fluorescent images of the 5CB indicated the presence of FITC-PAH (data not shown), consistent with formation of PAA/PAH films at the lipid-laden aqueous-5CB interface.

The results above are consistent with the formation of PEM films at the aqueous-5CB interface. The higher mobility of the polyelectrolytes at the aqueous-liquid crystal interface, as compared to their mobility on the conventional solid substrate, did not prevent the formation of the PEM film.

EXAMPLE 3

Orientational Order in the Liquid Crystal in Relation to the Formation of PEM Films This example demonstrates that the orientational order of the liquid crystal can be coupled to the formation of PEM films (FIG. 3B-E). Polarized light microscopy was used to characterize the orientational order within the liquid crystal, prepared as described in Example 1 above. The optical appearance of 5CB when immersed under water (no lipids or polyelectrolyes) was bright with pale yellow-pink interference colors (FIG. 3B). This appearance can be explained in the following manner: At the 5CB-glass interface, the orientation of the liquid crystal is anchored perpendicular to the glass due to the monolayer of octadecyltrichlorosilane (shown schematically in the director profile in FIG. 1). Consequently, the bright optical appearance of the liquid crystal is the result of in-plane birefringence of the liquid crystal aligned parallel to the aqueous-5CB interface. The presence of dark brushes emanating from points generally along the edges of each compartment indicates that there is a variation of the azimuthal (radial) orientation of the liquid crystal within each compartment of the grid. The deposition of a PEM consisting of ten bilayers of PSS/PAH led to only minor changes in the optical appearance of the liquid crystal when viewed under water (FIG. 3C). The differences observed (changes in the position of the dark brushes, for example) were also observed for controls in which water was repeatedly exchanged over the 5CB. The lack of change in the optical appearance of the liquid crystal suggests that both the process of PEM film formation and the presence of the PEM film itself do not significantly affect the orientations of the liquid crystal when in contact with water in this experiment. However, a coupling between the liquid crystal and PEM is evident when the PEM was removed from the water into air.

While the presence of a PEM film did not influence the anchoring of 5CB in contact with aqueous solutions, it was determined if the presence of the PEM film would be able to maintain the orientation of 5 CB if the 5 CB were removed from the aqueous environment and dried in air. In the absence of a PEM or lipid layer, 5CB showed the expected bright appearance (planar anchoring) in water (e.g., FIG. 3B), and the typical dark appearance (homeotropic anchoring) when subsequently dried in air (FIG. 3D). In contrast, 5CB on which ten bilayers of PSS/PAH had been deposited (formed directly at the aqueous-5CB interface) exhibited an optical appearance that was bright, corresponding to planar anchoring of the 5CB (FIG. 3E). This appearance was essentially unchanged by the drying process (compare FIGS. 3C and 3E). Fluorescence microscopy indicated a fairly uniform distribution of the top FITC-PAH layer of the PEM film on the 5CB (FIG. 3F). This result provides further evidence that PEM films form at the aqueous-5CB interface and demonstrates the robustness of the PEM film on the 5CB. In addition, this result indicates that a coupling exists between the orientations of 5CB and presence of a PEM film at the 5CB surface: The PEM preserved planar anchoring of the 5CB under conditions that would normally lead to homeotropic anchoring. Samples that were intentionally handled roughly to dislodge regions of the PEM film from the 5CB surface showed areas of planar anchoring, which corresponded to regions covered by the PEM film, and regions of homeotropic anchoring, which corresponded to areas in which the PEM had been removed (data not shown).

The coupling between PEM film formation on lipid-seeded aqueous-5CB interfaces and the order in the liquid crystal was also investigated. After depositing DLEPC at the aqueous-5CB interface, the optical appearance of 5CB changed from bright (e.g., FIG. 3B) to dark (FIG. 31) within ~1 min, indicating a change from planar to homeotropic anchoring of the 5CB. A similar transition has been observed for zwitterinic phospholipids, albeit at much longer timescales (~2 h), and has been shown to be the result of a coupling between adsorbed lipid and the liquid crystal. The homeotropic orientation of 5CB was maintained at least 30 min after replacing the lipid solution with lipid-free water. The appearance of the 5CB did not change after depositing ten PAA/PAH bilayers on the DLEPC-laden interface (FIG. 3J). Similar results were observed when the lipid layer was DLPS rather than DLEPC (data not shown).

EXAMPLE 4

Unsupported PEM Films are Stable after Removal of Supporting Liquid Layers

This example demonstrates the PEM films are stable after removal of the supporting liquid layers. Ten bilayers of PSS/PAH were deposited (formed directly at the aqueous-5CB interface) on 5CB hosted in a TEM grid, as described above. The 5CB exhibited an optical appearance that was bright, corresponding to planar anchoring of the 5CB (FIG. 3E). Next, and as described in Example 3, the 5CB was removed from the aqueous solution and dried. Fluorescence microscopy indicated a fairly uniform distribution of the top FITC-PAH layer of the PEM film on the 5CB (FIG. 3F). After preparing PEM films on 5CB and drying the samples in air, the inventors removed the TEM grid from the OTS-glass slide and immersed the grid-5CB-PEM sample in ethanol to dissolve the 5CB. After the ethanol evaporated, this process yielded PEM films that, while significantly damaged, spanned many of the TEM grid squares as freestanding PEM films (FIG. 3G-H).

EXAMPLE 5

PEMs Selectively Mediate Interactions Between Analytes and Liquid Crystals

Figure 4:
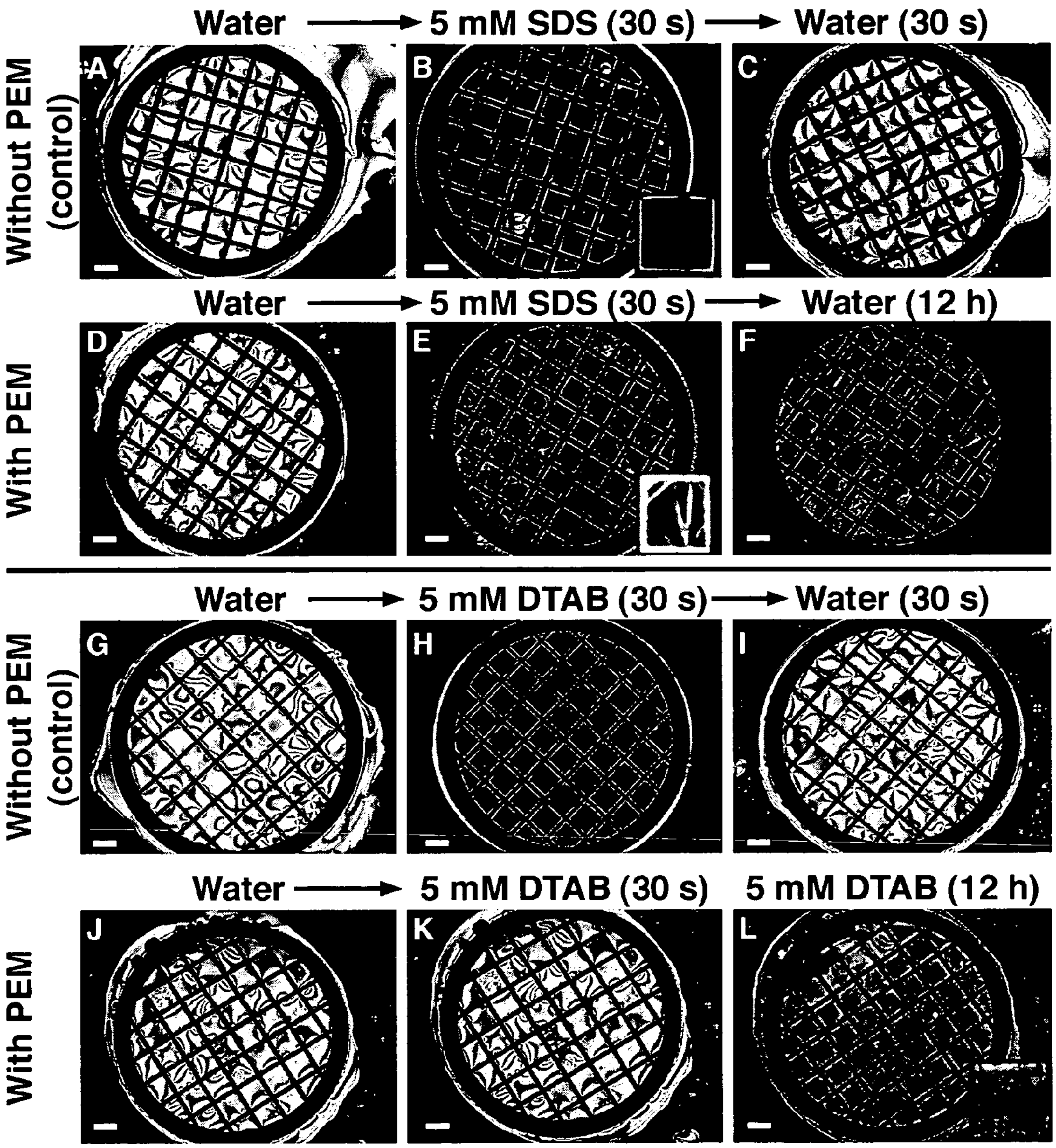
FIG. 4. PEM films mediate interactions between surfactants and liquid crystals. A-F) Optical images (crossed polars) of an uncoated aqueous-5CB interface (A-C) and an aqueous-5CB interface coated with ten PSS/PAH bilayers (D-F) in water (A, D), 30 s after exposure to 5 mM SDS (B, E) and after subsequently exchanging the solution for an SDS-free solution (C, F). Image in C) is after 30 s, image in F) is after 12 h. G-L) Optical images (crossed polars) of an uncoated aqueous-5CB interface (G-I) and an aqueous-5CB interface coated with ten PSS/PAH bilayers (J-L) in water (G, J), 30 s after exposure to 5 mM DTAB (H, K), 12 h after exposure to 5 mM DTAB (L), and 30 s after subsequently exchanging the solution for a DTAB-free solution (I). Scale bars are 300 μm.

This example demonstrates a PEM film's ability to mediate interactions between an analyte present in an aqueous solution and a liquid crystal upon which the PEM film is deposited. The inventors exposed aqueous-5CB interfaces decorated with PSS/PAH multilayer films to solutions of the surfactants sodium dodecyl sulfate (SDS) and dodecyltrimethylammonium bromide (DTAB). In the absence of a PEM film, the adsorption of either SDS or DTAB to aqueous-5CB interfaces is fast (seconds) and leads to a transition from planar to homeotropic orientation of the 5CB (FIG. 4A-B, G-H). When the bulk SDS or DTAB solution is replaced with a solution free of surfactant both SDS and DTAB desorb from the aqueous-5CB interface on the timescale of seconds and the 5CB orientation becomes planar (FIG. 4C, I).

The presence of a PEM film at the aqueous-5CB interface had no apparent influence on the adsorption of SDS to the interface, but changed the adsorption characteristics of DTAB. When the PEM-coated interface was exposed to 5 mM SDS, a transition from planar to homeotropic orientation of 5CB occurred on a timescale comparable to that without a PEM film present (FIG. 4D-E). However, when the inventors exposed a PEM-coated 5CB interface to a solution of 5 mM DTAB, they observed no transition from planar to homeotropic orientation of the 5CB, even after 12 h of exposure (FIG. 4J-L). Similar results were observed for 9.5 PSS/PAH bilayers (terminating in an anionic PSS layer, data not shown), suggesting that the phenomenon is not dependent on the electrostatic nature of the topmost PEM layer. While the PEM film showed no influence on the kinetics of SDS adsorption to the aqueous-5CB interface, the inventors observed the desorption kinetics to depend strongly on the presence of the PEM. The homeotropic orientation observed for 5CB coated with a PEM film and exposed to SDS solution was maintained for 12 hours after replacing the SDS solution with a SDS-free solution (FIG. 4F).

The presence of SDS creates a texture apparent in optical micrographs that are reminiscent of wrinkled fabric (FIG. 3E, inset). This type of texture was not observed when SDS was adsorbed to 5CB in the absence of a PEM film (FIG. 4B, inset). The presence of DTAB did not produce any obvious wrinkled texture of the PEM films, though there did appear to be a roughening in the appearance of the PEM-coated 5CB when exposed to DTAB for 12 h (FIG. 4L).

EXAMPLE 6

Formation of PEM Films at Liquid-Liquid Interfaces; Aqueous-Liquid Crystal Interfaces are Representative of Liquid-Liquid Interfaces The present invention contemplates formation of PEMs at liquid-liquid interfaces beyond aqueous-liquid crystal interfaces. One of skill in the art will appreciate that properties of aqueous-liquid crystal interfaces are representative of the broader class of liquid-liquid interfaces. For example, diffusion coefficients at aqueous-isotropic oil and aqueous-liquid interfaces have been demonstrated to be comparable. Fluorescence recovery after photobleaching (FRAP) measurements of the phospholipid dilauroylphosphocholine (DLPC) adsorbed at the aqueous-liquid crystal interface yielded diffusion coefficients of 6 to $15 \times 10^{-12}$ $m^2/s$ for DLPC at the water-liquid crystal interface (fluorescein-dipalitoylphosphocholine probe). [Brake et al. Langmuir 2005, 25:2218] Yu et al. measured DLPC diffusivity at a water-heptane interface to be $20 \times 10^{-12}$ $m^2/s$ (NBD probe). [Adalsteinsson, T.; Yu, H. Langmuir 2000, 16:9410.] These values demonstrate that the diffusion of lipids at aqueous-liquid crystal interfaces and aqueous-oil interfaces are comparable and substantiate the formation of PEM films across a broad range of liquid-liquid interfaces.

EXAMPLE 7

Formation of a PEM Film at an Aqueous-Isotropic Oil Interface

Figure 5:
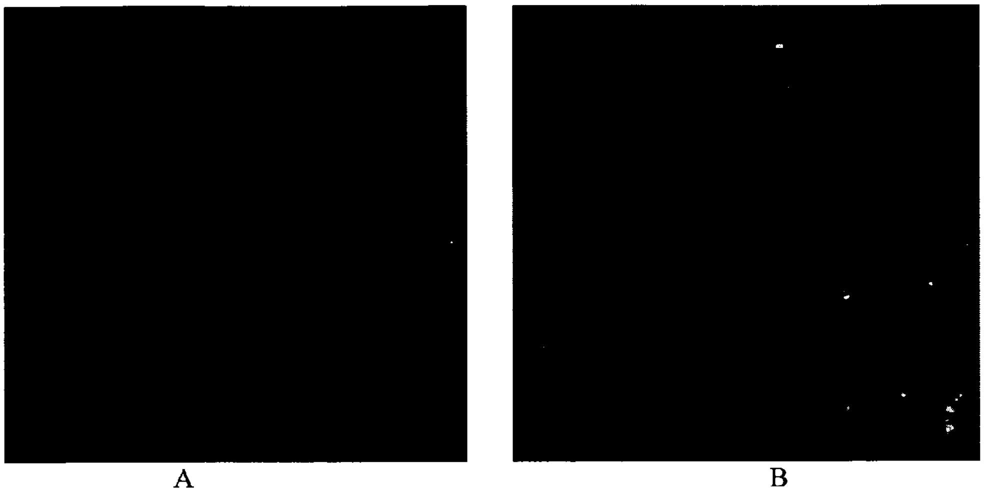
FIG. 5. Fluorescence images of A) silicon oil after deposition of 3 bilayers of PSS/PAH (no fluorescently-labeled polymer) are shown and, as well, B) silicon oil after deposition of 4 bilayers of PSS/PAH, the final PAH layer incorporating a fluorescently-labeled PAH polymer.

In order to further support the broad applicability of the present invention to the formation of PEM films generally at liquid-liquid interfaces, this example describes the formation of a PEM film at the interface between water and an immiscible silicon oil. The inventors prepared PEM films on the aqueous-silicon oil interface using substantially the same procedure previously-described in Example 1 above. After repeated exposure to alternating PSS and PAH solutions, and ending with a fluorescently-labeled PAH solution, a uniform bright fluorescence was observed that indicated the presence of a PEM film at the aqueous-silicon oil interface. FIG. 5 shows fluorescence images depicting this PEM formation at an oil-water interface. Specifically, FIG. 5 shows fluorescence images of A) silicon oil after deposition of 3 bilayers of PSS/PAH (no fluorescently-labeled polymer) are shown and, as well, B) silicon oil after deposition of 4 bilayers of PSS/PAH, the final PAH layer incorporating a fluorescently-labeled PAH polymer. The increase in fluorescence intensity demonstrates the formation of a PEM film at the aqueous-silicon oil interface. The presence of silicon oil was verified after the treatment by observing the edges of the oil film with brightfield microscopy.

EXAMPLE 8

Formation of a PEM Film on the Fluorinated Liquid Crystal TL205

Figure 6:
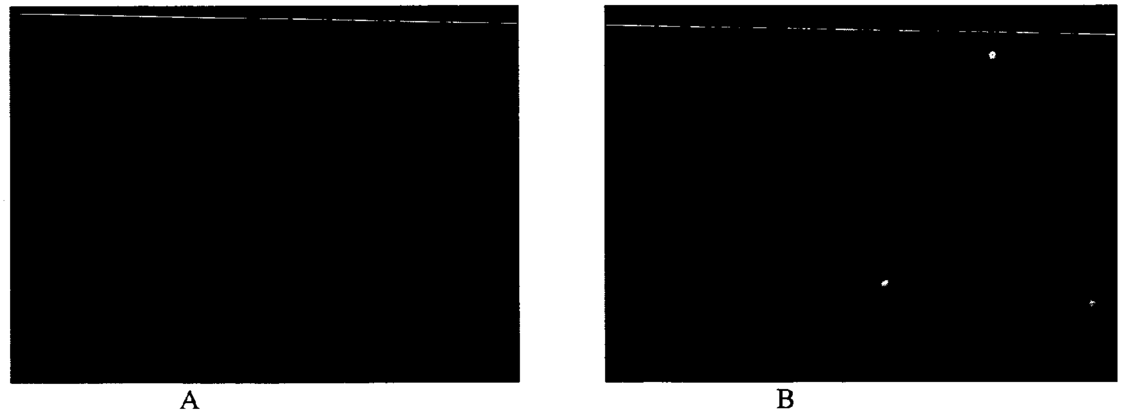
FIG. 6. Fluorescence images depicting 5 bilayers of PSS/PAH (two fluorescently-labeled PAH layers) at A) aqueous-5CB and B) aqueous-TL205 interfaces.

This example describes the formation of a PEM film on yet another liquid crystal, namely, the fluorinated liquid crystal TL205. A procedure as substantially described in Example 1 above was performed to provide a PEM layer at an aqueous-TL205 interface. Referring to FIG. 6, the PEM film was successfully formed at the aqueous-5CB interface as demonstrated by fluorescence images depicting 5 bilayers of PSS/PAH (two fluorescently-labeled PAH layers) at A) aqueous-5CB and B) aqueous-TL205 interfaces. The intensity on TL205 appears similar to that on 5CB, indicating that PEM film formation is similar on the two liquid crystals.

EXAMPLE 9

Characterization of Growth of PEM Films at Aqueous-LC Interfaces

In this example, the inventors describe a detailed characterization of the growth of PEM films at aqueous-LC interfaces. The growth characteristics of poly(sodium-4-styrenesulfonate) (PSS)/poly(allylamine hydrochloride) (PAH) and PAH/poly(acrylic acid) (PAA) multilayers formed at the LC-aqueous interface were investigated by covalently attaching fluorescent dyes to both PSS and PAH, and by comparing the growth characteristics on LCs to solids with hydrophilic and hydrophilic surfaces as a function of pH. Whereas the PEMs formed from PSS/PAH grow at the interfaces of LCs in a manner comparable to the growth on the surfaces of solids, the growth characteristics of PAA/PAH PEMs on LCs differ substantially from the solids investigated. While PAH/PAA films show no growth on hydrophobic OTS surfaces their growth at the LC-aqueous interface was much higher than that observed on the hydrophilic solid surfaces. The zeta-potential measurements of LC-aqueous interface also provides evidence for the presence of a small negative charge at these interfaces.

The inventors characterized the growth behavior of PSS/PAH multilayers at the 5CB-aqueous interface with the incorporation of fluorescent molecules in both cationic and anionic polyelectrolyte. The present study incorporated both FITC labeled PAH and Rhodamine labeled PSS with the aim of investigating the growth behavior of PSS/PAH films at the LC-aqueous interface and to provide evidences for PSS adsorption at the LC interface.

The present example illustrates the characteristic features of PEMs grown at the 5CB-aqueous interfaces and compares them to PEMs grown on solid substrates. In addition, a PEM system of PAH/poly (acrylic acid) (PAA) films formed at the 5CB-aqueous interface is described. Unlike PSS/PAH multilayer system, PAH/PAA films consist of both weak polyelectrolytes and hence shows a strong dependence on the pH of the polyelectrolyte solutions. These films formed at a pH combination of PAA(3.5)/PAH(7.5) are known to form very thick films and undergo a pH induced reorganization. Such properties of these films make them useful for the control of the interfacial properties of the LC interface.

The growth of the PSS/PAH and PAH/PAA multilayer systems at the 5CB-aqueous interface as compared to that on the hydrophobic and hydrophilic solid surfaces led to the identification of differences in growth behavior of these multilayer systems. While PSS/PAH films grow at the 5CB-aqueous interface in a manner comparable to hydrophobic and hydrophilic solid substrates, PAH/PAA films grow at a higher rate at the LC-aqueous interface as compared to hydrophilic solid substrates and do not grow on hydrophobic substrates. This example lastly describes the nature of the LC-aqueous interface for being charged or hydrophobic in nature by performing zeta-potential measurements of the LC in water emulsions.

PEM formation at the LC-aqueous interface not only facilitates the use of this system for biological sensing by providing a functional and responsive substrate unlike a solid substrate but also for the study of other events such as pH or salt induced molecular rearrangements in the polyelectrolyte film or the diffusion of molecules known to cause ordering transition of LCs through PEMs formed by various polyelectrolyte systems. LC-aqueous interfaces provide a unique platform for PEM growth due to their mobile nature on which various events such as reorganization and molecular diffusion are expected to take place more selectively.

Figure 7:
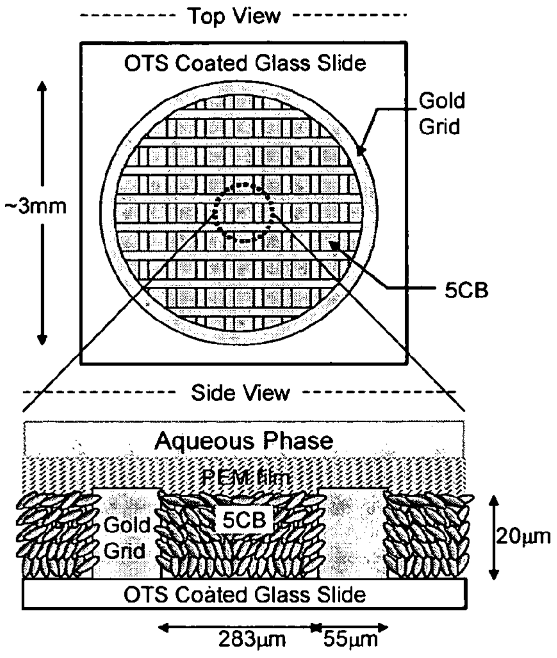
FIG. 7. a) Schematic illustration of the experimental geometry used to prepare planar interfaces between aqueous phases and immiscible thermotropic liquid crystals. PEMs form at the LC-aqueous interface and the LC shows planar anchoring at such interfaces. b) Structures of the molecules used in this work: the liquid crystal 5CB, repeat units of PSS, PAA, PAH, FITC-PAH and Methacryloxyethyl thiocarbamoyl rhodamine B copolymerized with PSS.
Figure 7:
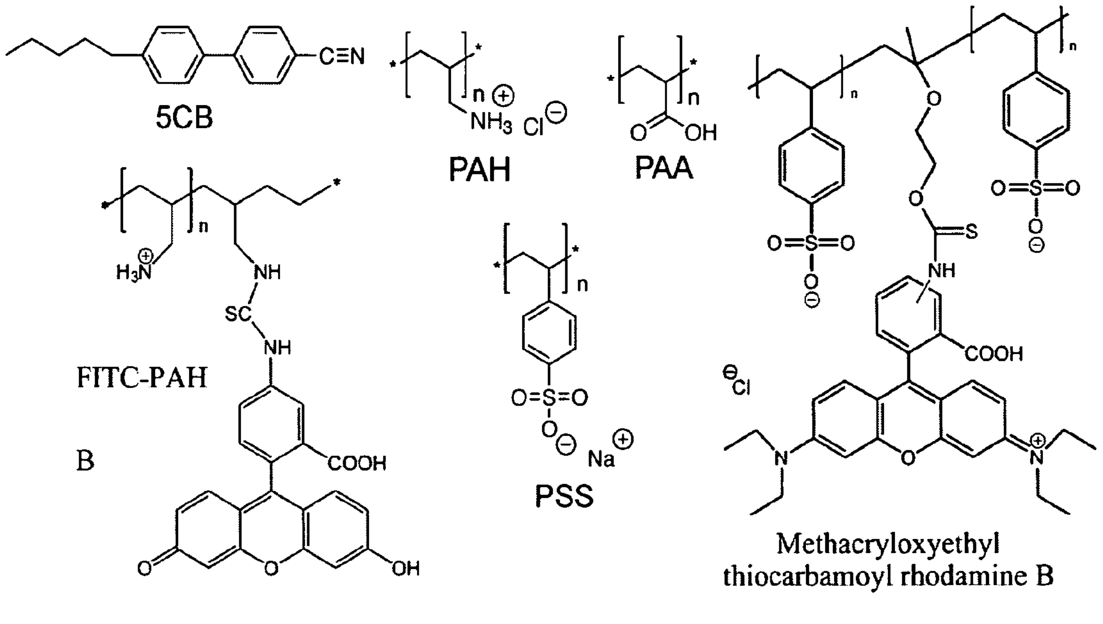

FIGS. 7A and 7B show the experimental set-up and materials used in this study respectively. The goal of the experiment reported in FIG. 8 was to determine the growth characteristics of PEMs of PAH/PSS formed at the interface between an aqueous phase and 5CB. In contrast to experiments where the pH of the aqueous electrolyte containing PAH was not controlled, the experimental results reported in FIG. 8 were obtained at pH 8. The results reported in FIG. 8 use FITC-PAH with PSS, and PAH with Rh-PSS. In each of the experiments reported in FIG. 8, the interface was first contacted with PSS or Rh-PSS. While the fluorescence is measured after the deposition of PSS-Rh in FIG. 8A, it is measured after the deposition of FITC-PAH in FIG. 8B. For all the experimental measurements described in this example the error bars are calculated as the standard deviation obtained from 2 to 3 independent measurements with multiple samples at a time.

Figure 8:
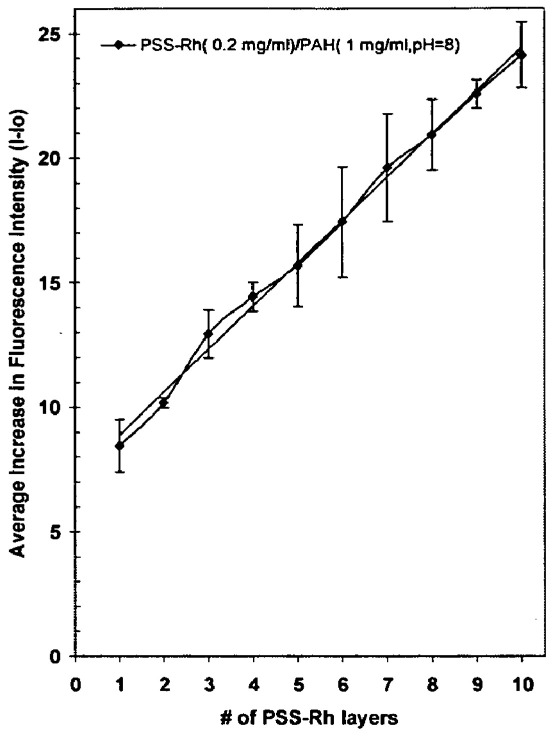
FIG. 8. Quantification of the growth of PSS/PAH multilayers at the 5CB-aqueous interface: Average increase in fluorescence intensity of (A) Methacryloxyethyl thiocarbamoyl rhodamine B labeled PSS for PSS-Rh/PAR (pH=8) PEMs and of (B) FITC labeled PAH measured for PSS/FITC-PAH (pH=8) PEMs grown at the 5CB-aqueous interface. Linear fits show the linear growth of the fluorescence intensity in both the cases.
Figure 8:
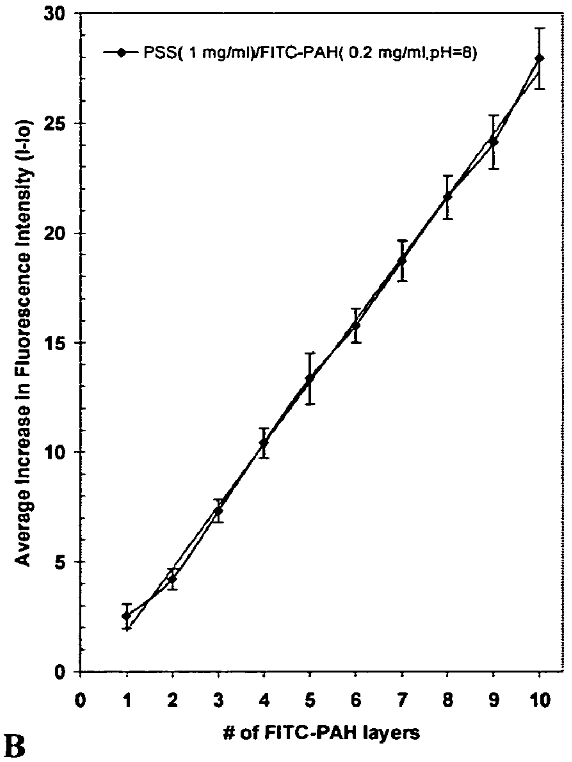

Inspection of FIG. 8 reveals that the growth in fluorescence of rhodamine in FIG. 8A and FITC in FIG. 8B is linear with number of layers deposited at the interface. The absolute values of fluorescence intensity can not be compared between FIGS. 8A and 8B because the measurements were performed with different fluorophores as well as imaging conditions.

Figure 3:
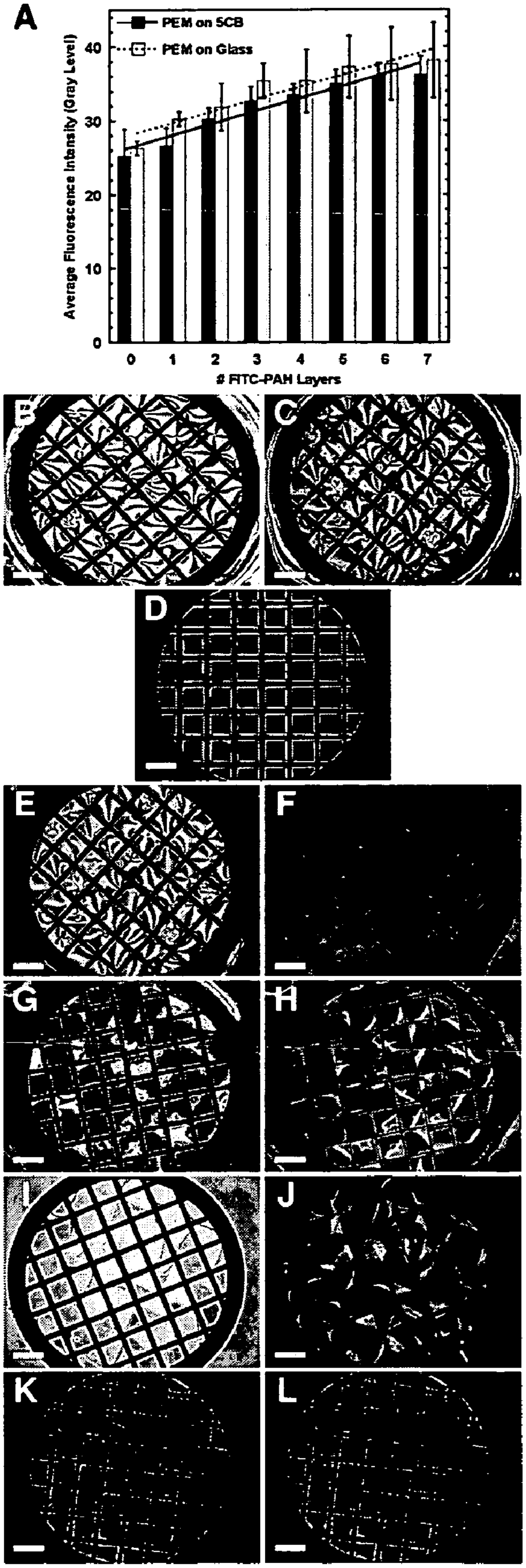
FIG. 3. Evidence for the formation of PEMs at aqueous-liquid crystal interfaces. A) Quantification of the linear buildup of PEM layers using the fluorescence intensity of FITC-labeled PAH. B-C) Optical images (crossed polars) of 5CB in contact with water before (B) and after (C) deposition of 10 PSS/PAH bilayers directly on the aqueous-5CB interface. D) Optical image (crossed polars) of 5CB placed in water and subsequently dried in air, for comparison to E. E-F) Optical (crossed polars, E) and fluorescent (F) images of 10 PSS/PAH bilayers formed at the aquous-5CB interface and subsequently dried in air. G-H) Brightfield (G) and fluorescent (H) images of 10 PSS/PAH bilayers formed at the aqueous-5CB interface that has been dried in air, placed in ethanol to remove the 5CB, and dried, demonstrating freestanding PEM films. I-J) Optical images (crossed polars) of 5CB coated with a monolayer of DLEPC (I) and after deposition of 10 PAA/PAH bilayers on the DLEPC-decorated interface (J). Scale bars for all images are 300 μm.

Whereas the rate of growth of fluorescence from FITC-PAH in FIG. 3 appears to decrease after $8^{th}$ bilayer, such a decrease in rate of growth of the PEM is not seen in FIG. 8*b*. The experiments reported herein were performed using PAH solutions adjusted to pH=8, whereas the solutions used in the previous experiments shown in FIG. 3 were performed using aqueous solutions of PAH that were not adjusted to pH 8.

The increase in fluorescent intensity relative to the background after the exposure of PSS-Rh to the 5CB-aqueous interface indicates the adsorption of PSS-Rh at the 5CB-aqueous interface. Also it should be noted that the increment in fluorescence intensity associated with the deposition of the first layer of PSS-Rh was greater than the increment in fluorescence intensity associated with deposition of subsequent layers of Rh-PSS. This result suggested that the amount of Rh-PSS adsorbed onto the interface of the 5CB (first layer) is greater than the amount of Rh-PSS deposited onto the PEM. In contrast, the increment in fluorescence upon deposition of the first layer of FITC-PAH is similar to subsequent layers. The first layer of FITC-PAH is not adsorbed directly onto the aqueous interface of the 5CB but is adsorbed onto a PSS-decorated interface of 5CB.

Figure 9:
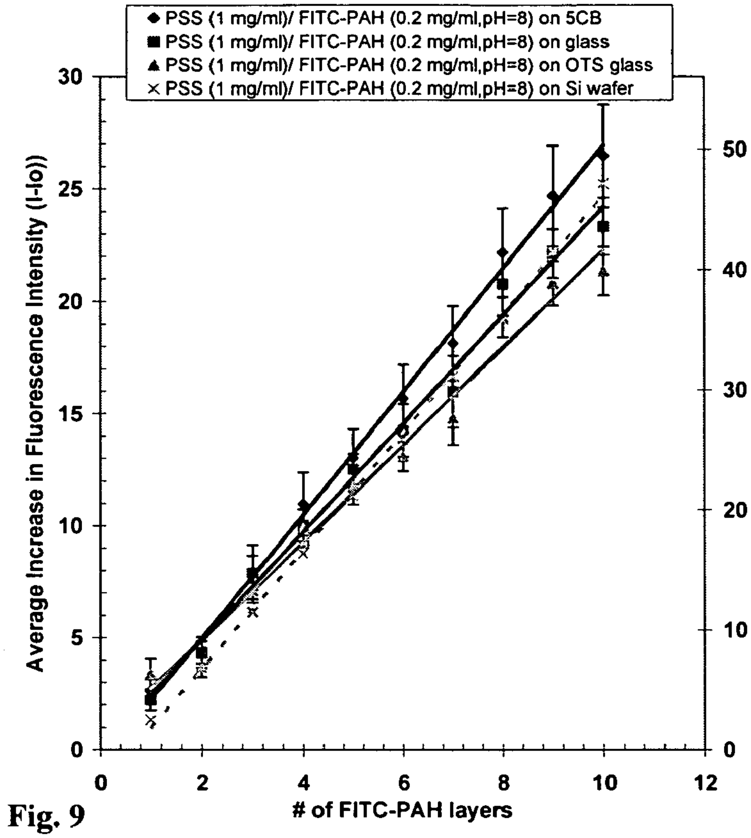
FIG. 9. Comparison of growth of PSS/PAH PEMs grown at the 5CB-aqueous interface Vs hydrophobic and hydrophilic solid substrates: Average increase in fluorescence intensity of FITC labeled PAH measured for PSS/FITC-PAH (pH=8) films grown at the 5CB-aqueous interface, clean glass and OTS coated glass. To get an estimate for the films thickness on 5CB, the right side Y-axis indicates the average increase in ellipsometric thickness of PSS/PAH (pH=8) films grown on Si wafer.

The goal of the experiments shown in FIG. 9 was to compare the growth characteristics of PSS/PAH multilayers at the 5CB-aqueous interface with growth of PSS/PAH multilayers prepared on hydrophobic and hydrophilic solid substrates. The multilayers were grown on OTS-treated glass and clean glass surfaces using the same set of polyelectrolyte and solution conditions used to obtain the data in FIG. 8. The starting layer for the 10 bilayer system was PSS for all experiments.

Figure 13:
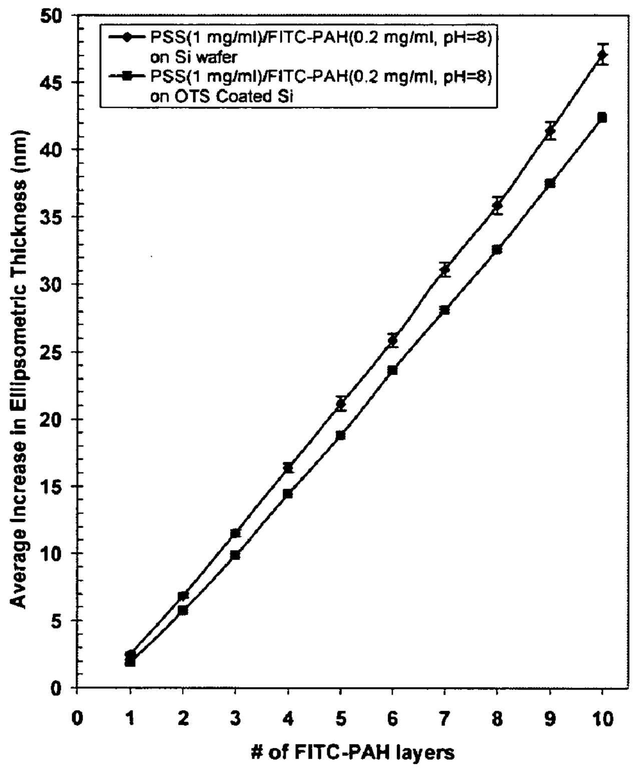
FIG. 13. Average increase in ellipsometric thickness of PSS/PAR films (pH=8) grown on hyrdophilic silicon substrate and OTS coated silicon wafer.

FIG. 9 shows the increase in fluorescence for the PSS/FITC-PAH films grown at the interface of 5CB, clean glass and OTS-treated glass. From FIG. 9, it is observed that: (a) a linear growth of fluorescence is seen at all three interfaces; (b) the rate of growth of fluorescence is similar on all three interfaces, although the rate is slightly higher at the 5CB-aqueous interface than OTS-treated glass; (c) independent ellipsometric measurements (see FIG. 13) show that growth of the PEMs is slightly higher on native oxide surfaces than OTS-treated surfaces which is consistent with the observations obtained from fluorescence measurements (on the right side of FIG. 9, the inventors have plotted the ellipsometric thickness of the PEM obtained at the native oxide surface). Because the growth of fluorescence for all the PEMs in FIG. 9 is similar, the ellipsometric thicknesses obtained at the native oxide surface can be used to estimate the thicknesses of the PEMs of PSS and PAH formed at the aqueous-LC interface. These results suggest that PEMs of PSS and PAH with thicknesses between 5 nm and 50 nm can be formed at aqueous-LC interfaces.

Figure 10:
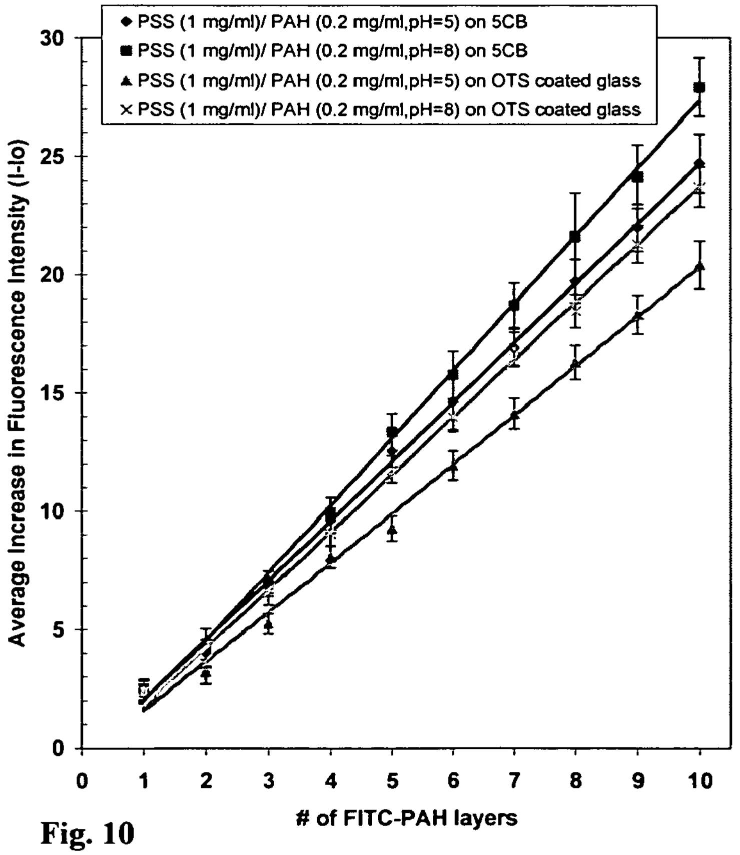
FIG. 10. pH dependence growth of PEM of PSS/FITC-PAH on hydrophilic silicon substrate, hydrophobic OTS coated silicon and 5CB-aqueous interface: Average increase in fluorescence intensity of FITC labeled PAH measured for PSS/FITC-PAH (pH=5 or 8) at 5CB-aqueous interface and OTS coated glass FIG. 11. (a) Quantification of the growth of FITC-PAH/PAA PEMs at the 5CB-aqueous interface, hydrophilic native oxide glass and hydrophobic OTS coated glass: Average increase in the fluorescence intensity of FITC labeled PAH measured for FITC-PAH(7.5)/PAA(3.5) PEM and for FITC-PAH(6.5)/PAA(6.5) PEM grown at the 5CB-aqueous interface, hydrophilic native oxide glass and hydrophobic OTS coated glass for 1 mg/ml concentrations of FITC-PAH.

The experiments reported in FIG. 10 sought to characterize the effect of the pH of the weak polyelectrolyte PAH on the growth of PSS/PAH PEMs at the 5CB-aqueous interface. As previously-reported, the pH of an aqueous solution of the weak polyelectrolyte PAH influences the growth of PSS/PAH multilayers on the surfaces of solids. At pH below 7, PAH in solution is largely protonated, whereas at pH's higher than 7 it becomes partially charged with its charge getting reduced to 88% of the maximum charge at a pH of 8 in PEM environment (with no salt used). To test whether a 5CB-aqueous interface behaves similar to a solid substrate, showing similar growth trends at different pH, the inventors chose a pH of 5 (fully charged) and 8 (partially charged) for FITC-PAH solution for PSS/FITC-PAH multilayer formation. In the multilayer formation at the 5CB-aqueous interface, the weak polyelectrolyte solutions of FITC-PAH was maintained at a pH of either 5 or 8, while the pH of strong polyelectrolyte, PSS (pH=5.58) was not adjusted. The base layer for the different substrates being the same as described above. It is important to note that although the fluorescence of FITC-PAH is known to vary with pH, all fluorescence measurements were performed immediately after rinsing the PEMs for 5 min at the pH (5.5-6.5) of rinsing water.

Figure 14:
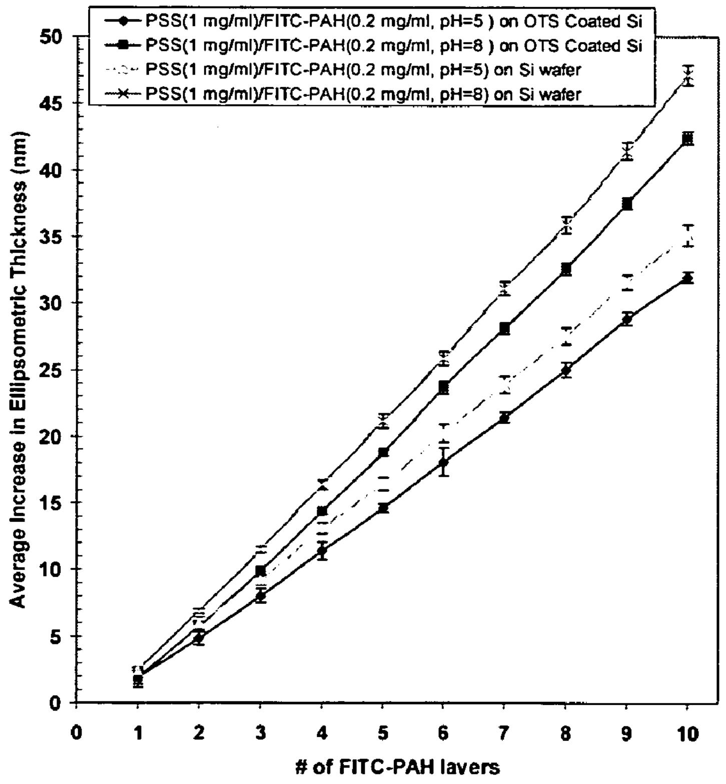
FIG. 14. Ellipsometric thickness of PSS/FITC-PAH films (pH=5 or 8) grown on OTS coated silicon & hyrdophilic silicon substrate.

FIG. 10 shows measurements of the growth of fluorescence of PEMs prepared from FITC-PAH and PSS at the interface of 5CB at pH 5 or 8. From FIG. 10, it is observed that: the rate of growth of fluorescence is greater at pH 8 than pH 5, consistent with prior reports of the effect of pH on growth of this PEM system. As shown in FIG. 14 the inventors also used ellipsometry to verify that the effect of pH on PEM growth on native oxide and OTS-treated surfaces are similar. As shown in FIG. 10, the magnitude of the effect of pH on the growth of the PEM at the interface of the 5CB is different from the effect of pH on the growth of the same PEM at the interface of OTS-treated glass. Not only the effect of pH is smaller but also unlike OTS coated glass the difference is only observed after 8-9 bilayers in the case of multilayers grown at the 5CB-aqueous interface.

The results in FIG. 10 demonstrate that the pH of the PAH solution does not influence the growth behavior of PSS/FITC-PAH multilayer films at the LC-aqueous interface, thought the presence of a small effect may not be reflected because of the large error bars associated with the measurements with LCs. With a controlled pH of 5 and 8 of the FITC-PAH solution, a linear growth trend is observed for the multilayers formed at the 5CB-aqueous interface. The multilayers were observed to be thicker for a PAH solution pH of 8 than a pH of 5 for all the substrates studied.

Figure 11:
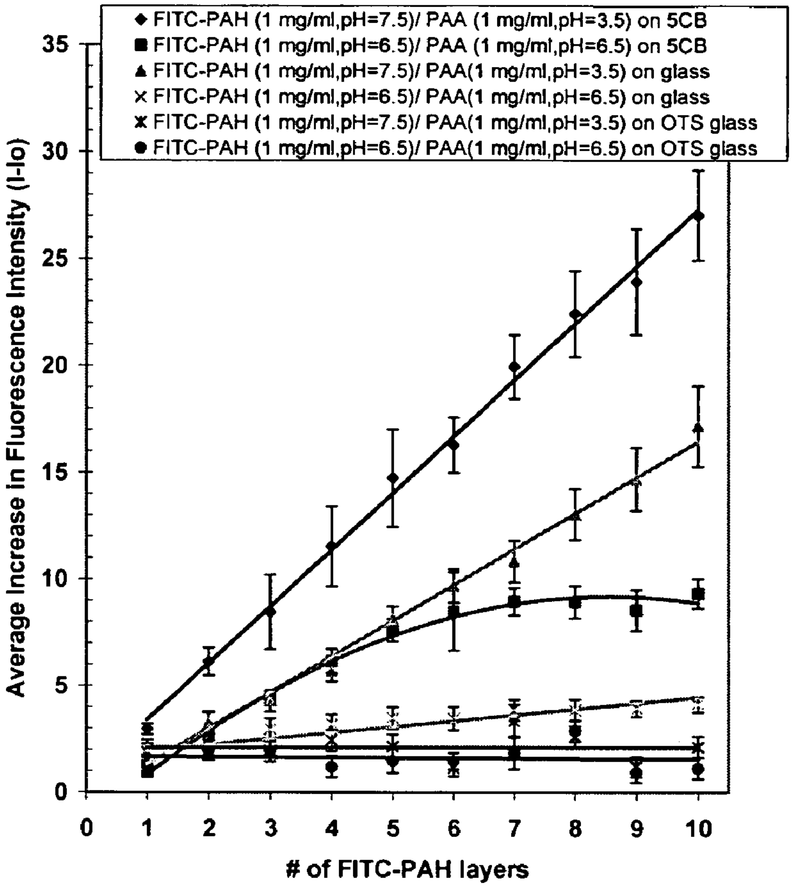

The experiment reported in FIG. 11 sought to characterize growth of FITC-PAH/PAA multilayers formed at the 5CB-aqueous interface. The growth of weak polyelectrolyte multilayers of FITC-PAH/PAA on a solid substrate is known to be highly pH dependent. With variation in pH, the charge density of the polyelectrolyte changes and hence different thicknesses of films are obtained after layer by layer deposition. Similar to the above investigations for PSS/PAH multilayer films formed at the 5CB-aqueous interface, here the inventors first established the growth trend for FITC-PAH/PAA multilayer films formed at the 5CB-aqueous interface. Second, the inventors compared the growth of FITC-PAH/PAA multilayers formed at the 5CB-aqueous interface with those formed on solid substrates; and third, The effect of two different pH combinations & polyelectrolyte concentrations on the multilayer film growth was investigated.

In the process of multilayer formation, the 5CB-aqueous interface was gently exposed first to FITC-PAH (1 mg/ml or 0.2 mg/ml, pH=7.5 or 6.5) for 15 min and then subsequently exposing the interface to poly acrylic acid (PAA, 1 mg/ml, pH=3.5 or 6.5) for 15 min after rinsing and this sequential procedure was repeated for 10 bilayers. To investigate the FITC-PAH/PAA PEMs formation on 5CB, two different pH systems were chosen, (a) FITC-PAH(7.5)/PAA(3.5)—which is known to show a significant pH induced thickness transition and (b) FITC-PAH(6.5)/PAA(6.5)—which forms very thin layers because of the fully charged state of the polyelectrolyte. To further investigate the nature of the growth of PAH/PAA-multilayers grown at the 5CB-aqueous interface as compared to solid substrates, multilayers were grown on hydrophilic native oxide glass and hydrophobic OTS coated glass with similar set of polyelectrolyte solutions as used for 5CB-aqueous interface.

FIG. 11 shows the increase in fluorescence for the FITC-PAH/PAA films grown at the interface of 5CB, clean glass and OTS-treated glass for two different pH systems. In all the cases FITC-PAH is the starting layer. It is evident from FIG. 11 that PAH/PAA multilayers grow for different pH combinations of polyelectrolyte at the 5CB-aqueous interface. Inspection of FIG. 11 (for data corresponding to 5CB-aqueous interface) reveals an approximately linear growth of fluorescence for 7.5/3.5 system while for 6.5/6.5 system the fluorescence increases up to $7^{th}$ bilayer and then remains almost constant. FIG. 11 also provides with the evidence of PAH adsorption at the 5CB-aqueous interface.

Figure 15:
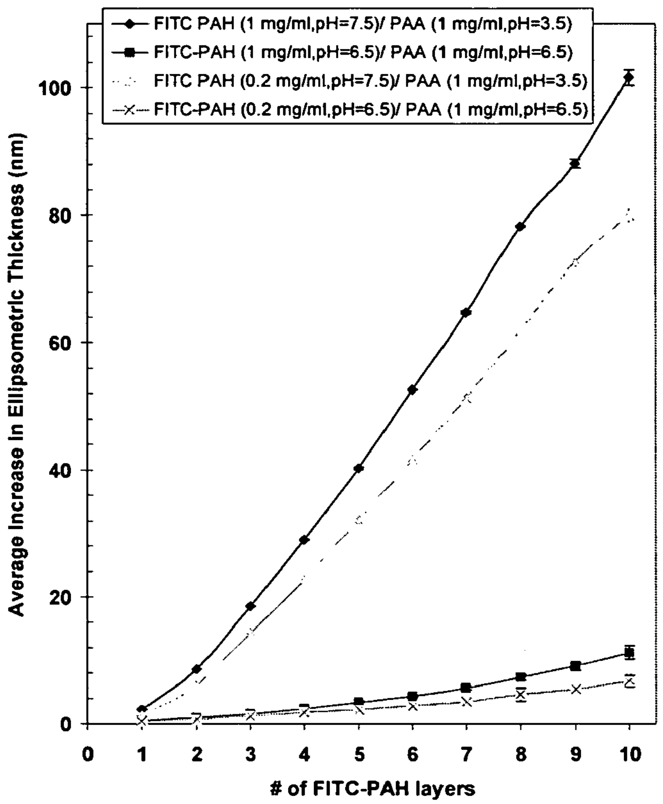
FIG. 15. Average increase ellipsometric thicknesses of FITC-PAH(7.5)/PAA(3.5) and FITC-PAH(6.5)/PAA(6.5) PEM on hydrophilized silicon substrate at two different concentration of 0.2 mg/ml and 1 mg/ml of FITC-PAH used for growing multilayer.

It can be observed from FIG. 11 that PAH/PAA multilayers grown at different pH combinations show different rate of growth of fluorescence at the interface of 5CB. Inspection of FIG. 11 reveals that the rate of growth of fluorescence (for data corresponding to 5CB-aqueous interface) at pH 6.6/6.5 is less than pH 7.5/3.5. This result is qualitatively consistent with past reports of the effect of pH on the growth of these PEMs. (FIG. 15 shows ellipsometric measurements of the effect of pH on the growth of this PEM system on a native oxide surface under the same conditions used to obtain data for the multilayers grown at the 5CB-aqueous interface.) Inspection of growth pattern of FITC-PAH/PAA multilayers on a native oxide surface reveals a qualitative trend that is similar to that obtained for the 5CB-aqueous interface, in that the ellipsometric thickness of the PEM deposited at pH 7.5/3.5 is greater than pH 6.6/6.5.

Inspection of FIG. 11 (for data corresponding to 5CB-aqueous interface and native oxide glass) reveals that rate of increase of fluorescence for multilayers achieved in the case of 5CB-aqueous interface is much higher than that obtained on native oxide surface. This indicates that the incorporation of fluorescent polyelectrolyte is more at the 5CB-aqueous interface than the native oxide surface. Closer inspection of FIG. 11 also reveals that the ratio of fluorescence intensities obtained using PEMs deposited at pH 7.5/3.5 versus pH 6.5/6.5 at interfaces of glass is larger than for the interface of 5CB.

FIG. 11 (for data corresponding to OTS coated glass) further illustrates the growth behavior of PAH/PAA films on the OTS coated hydrophobic glass surface. These measurements reveal that these PEMs do not grow on OTS-treated glass, emphasizing that the growth of these PEMs at the interfaces of 5CB is significantly different from solid, hydrophobic surfaces. The inventors observed the formation of an initial layer of FITC-PAH on the OTS coated glass but layers do not deposit further to form multilayers. This result is in line with previously reported results. The adsorption of PAH on the hydrophobic surface of OTS coated glass can be attributed to the negative zetapotential of OTS coated surface (reported in literature) or adsorption of hydrophobic polyelectrolyte PAH in the hydrophobic environment of OTS SAMS.

Figure 16:
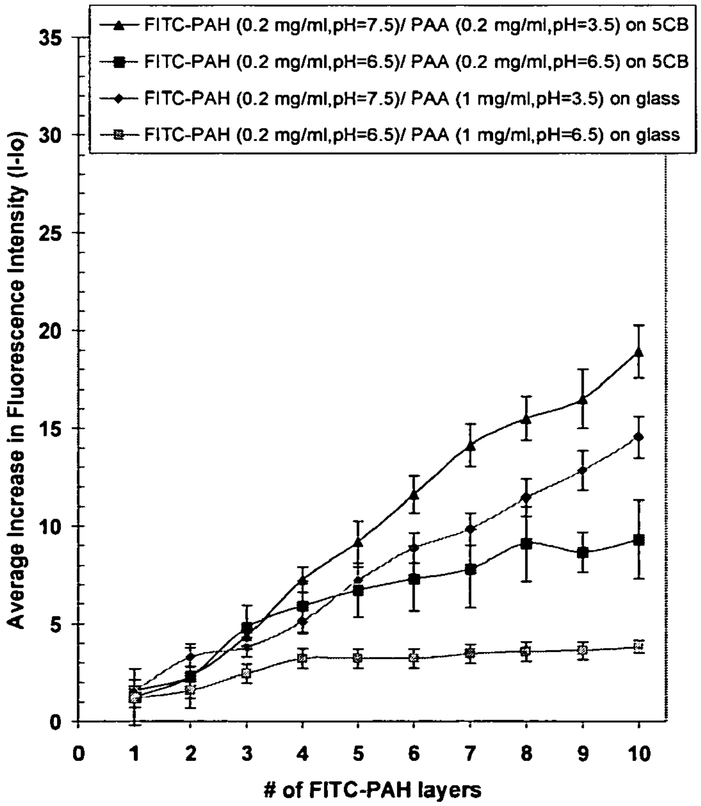
FIG. 16. (a) Quantification of the growth of FITC-PAH/PAA PEMs at the 5CB-aqueous interface and hydrophilic native oxide glass: Average increase in the fluorescence intensity of FITC labeled PAH measured for FITC-PAH(7.5)/PAA (3.5) PEM and for FITC-PAH(6.5)/PAA(6.5) PEM grown at the 5CB-aqueous interface and hydrophilic native oxide glass for 0.2 mg/ml concentrations of FITC-PAH.

To further compare the growth characteristics of PEMs on interfaces of 5CB to surfaces investigated in the past, the inventors report in FIG. 11 and FIG. 16 the effect of concentration of the polyelectrolytes (0.2 mg/ml to 1 mg/ml). These experiments reveal the effect of concentration of the polyelectrolytes on the growth of the PEMs at pH 7.5/3.5 appears to be qualitatively similar but a little greater on the interface of 5CB (FIG. 1) than native oxide (FIG. 15) or glass (FIG. 11 and FIG. 16) surfaces.

In summary, PAH/PAA multilayers do grow at the 5CB-aqueous interface and unlike PSS/PAH PEMs, PAH/PAA multilayer films show different growth characteristic at the 5CB-aqueous interface as compared to solid surfaces. While PSS/PAH multilayers grow at the 5CB-aqueous interface in a manner comparable to hydrophobic and hydrophilic solid substrates, PAH/PAA multilayer show significant differences. PAH/PAA multilayers at the 5CB-aqueous interface grow at a rate which is much higher as compared to the growth on the hydrophilic native oxide glass surface but these multilayers simply do not grow on the hydrophobic OTS coated glass surface for the mentioned solution conditions.

The results above indicate that the growth of PEMs on aqueous interfaces of 5CB differ from both native oxide/glass and hydrophobic surfaces. Perhaps most striking is the observation that PEMs of PAA and PAH grow at interfaces of 5CB under conditions for which they do not grow at hydrophobic surfaces (FIG. 11). It is also interesting that the results above suggest that PAH adsorbs directly to the interface of the 5CB.

Figure 12:
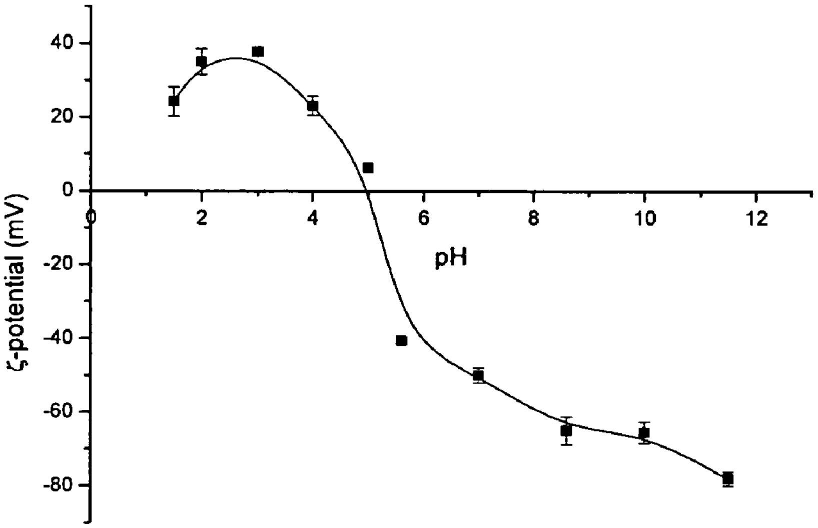
FIG. 12. Variation of zeta potential with pH of a 5CB-aqueous interface.

Inspection of FIG. 12 reveals that the zeta potential of the interface of 5CB at pHs above 5 is negative. The origin of the negative zeta potential is likely because of the strong adsorption of the hydroxyl ions at the 5CB-aqueous interface. The fact is further supported by the variation of zetapotential of 5CB-aqueous interface with pH as shown in FIG. 12. This observation likely underlies the conclusion above that PAH adsorbs directly to 5CB (via electrostatic interactions and via the adsorption of hydrophobic polycation PAH in the hydrophobic environment of 5CB). The results disclosed herein demonstrate that PSS/PAH and PAH/PAA multilayer films can be formed at the mobile 5CB-aqueous interface.

For the case of PSS/PAH multilayers, the comparison reveals that the 5CB-aqueous interface shows similar trends for the multilayer growth as shown by solid substrates. Although the PAH/PAA multilayers reveals a growth trend at the LC-aqueous interface that resembles hydrophilic solid but it differs significantly from solid hydrophobic surfaces. While PAH/PAA multilayer films do not grow on hydrophobic OTS coated surfaces they grow significantly at the 5CB-aqueous interface unlike the case of PSS/PAH multilayers. The growth of PAH/PAA films is also much higher at the 5CB-aqueous interface as compared to hydrophilic solid substrates. Also, various factors like polyelectrolyte pH and solution concentration affect the film growth in a slightly different manner as they do for solid substrates.

Zeta-potential measurements performed on the 5CB-aqueous interfaces indicate the presence of small negative charge at these interfaces (FIG. 12) at pH values greater than about 5. The results thus obtained provides a firm ground for the future research which is focused on using LCs in conjunction with PEMs to serve as amplifiers and transducers for various molecular events, thus providing approaches to the design of a range of materials with potential technological applications in high throughput screening, drug delivery, and chemical and biological sensing.

EXAMPLE 10

Formation of Biomolecule-Containing PEMs at Aqueous-LC Interfaces to Report the Presence and/or Activity of Biomolecules The coupling between LCs and PEMs that incorporate biomolecules provides opportunities to report the presence and activity of biomolecules. For example, the coupling can be used to: 1) observe the transport of active enzymes through PEM films; 2) monitor the digestive activity of enzymes on PEM films that incorporate proteins; and 3) tailor PEM films to facilitate detection of the presence and activity of protein toxins such as botulinum toxin in solution.

Figure 17:
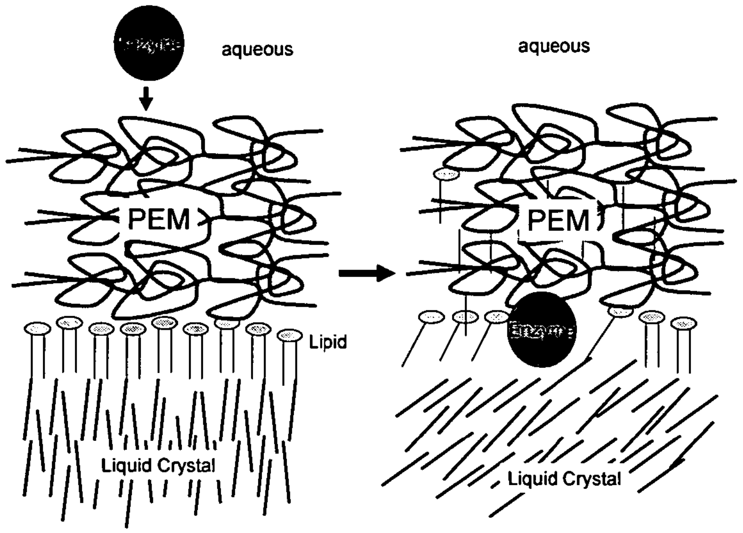
FIG. 17. Schematic illustration of a PEM supported on a lipid-decorated surface of a LC. Transport of the enzyme across the PEM is reported by the change in orientation of the LC that accompanies the enzymatic degradation of the lipid.

Transport of Enzymes to Substrates Hosted at Interfaces of LCs. Phosphlipase A2 ($PLA_2$) and DLPC may be used as a model system to demonstrate that PEM films can mediate the transport of enzymes from solution to the aqueous-LC interface. First, PEM films are prepared from PSS and PAH at aqueous-5CB interfaces that are decorated with DLPC (FIG. 17). DLPC is dilaurylphosphatidylcholine. The number of layers of PSS and PAH is varied from 0-10 in order to determine the number of layers that will prevent transport of the $PLA_2$ to the interface. The arrival of the enzyme at the DLPC-decorated interface of the LC is reported by an orientational transition associated with the enzymatic hydrolysis of the DLPC.

Past studies demonstrate that the permeability of proteins (IgGs) through PEMs can be increased through the incorporation of proteins into the PEMs. PEMs prepared from PSS and IgGs may be used to show that the incorporation of IgG into the PEM permit permeation of the $PLA_2$ to the interface under conditions for which PEMs formed from PSS and PAH do not permit permeation. Again, the orientational ordering of the LCs is reported by the arrival of active enzyme at the interface.

PAA-PAH PEM films that are known to reorganize in response to changes in ionic strength. These films can be used to control the transport of enzymes to the aqueous-LC interface. DLPC can be deposited at the aqueous-5CB interface and then PEM films prepared from PAA and PAH on 5CB. The films are incubated at high ionic strength in order to introduce porosity. The films can be exposed to solutions of $PLA_2$ and changes in the appearance of the 5CB monitored to determine the extent of transport of the $PLA_2$ across the porous film.

Protein-containing PEM Films as Reporters of Enzyme Activity. Whereas the above paragraphs address the transport of proteins through PEMs by using anchoring transitions of the LCs, PEMs which host enzymes and are formed on the surfaces of LCs offer opportunity to create materials for biological sensors. Such materials are illustrated through descriptions of examples that involve incorporation of $PLA_2$ into PEMs formed on LCs.

Figure 18:
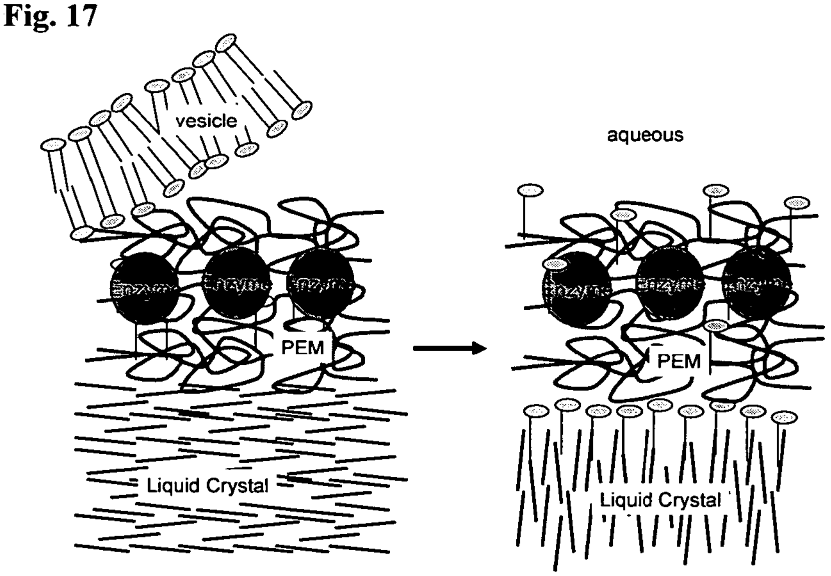
FIG. 18. Schematic illustration of a PEM formed using an enzyme as one component: upon exposure of the PEM to a vesicle, the enzyme cleaves the components of the vesicle and the flux of products of the enzymatic degradation diffuse to the surface of the LC.

Past studies demonstrate that it is possible to incorporate proteins into PEMs. As depicted in FIG. 18, phospholipid substrates for $PLA_2$ that are associated into vesicles will not permeate the PEMs (due to their size) whereas the products of enzymatic degradation will dissociate from the vesicles and form aggregates that are sufficiently small to be able to permeate the PEMs. This difference in permeability of the lipids makes it possible to report the presence of the products of the enzymatic reaction by their permeation through the PEM and associated orientational transition of the LC. The location of the enzyme within the PEM can be varied from the outer-most layer (highest accessibility to vesicles) to 1-6 layers beneath the outermost layer.

Figure 19:
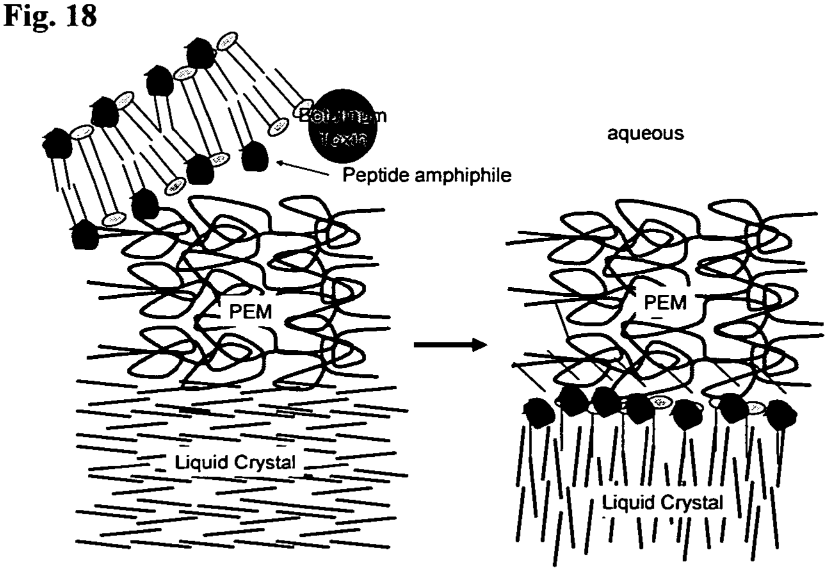
FIG. 19. Schematic illustration of reporting of botulinum toxin using PEMs and LCs. The products of the reaction catalyzed by BoNT/A can permeate the PEM leading to orientational changes in the LCs.
Figure 20:
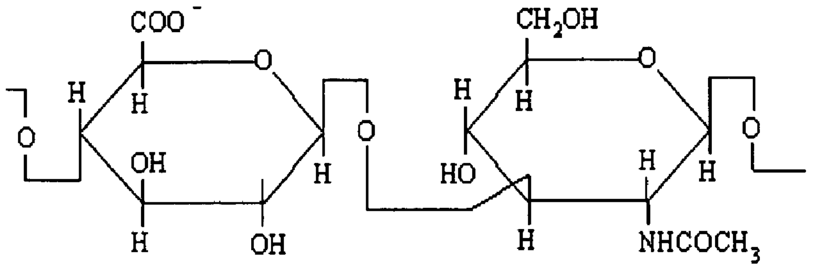
FIG. 20. Chemical structure of the repeating sequence in HA.

Reporting Activity of Botulinum Toxin. This example describes the use of PEMs formed on LCs for detection of botulinum neurotoxins (BoNTs). BoNTs cause paralysis by cleaving proteins involved in acetylcholine release and are among the most potent of biological toxins. This example uses a 19 amino-acid peptide sequence from SNAP-25, a synaptosomal protein that has been identified as a substrate for BoNT/A. Experiments are performed using the light chain of BoNT/A, which catalyzes the cleavage of SNAP-25. As shown in FIG. 19, (i) double-tailed peptide-amphiphiles from the 19 amino acid sequence of SNAP-25 is incorporated into vesicles of DLPC that do not permeate a PEM (e.g., PSS/PAH) formed at the surface of a LC, (ii) the light chain of BoNT/A is introduced into the aqueous phase, and (iii) cleavage of the peptide-amphiphile leads to its transport through the PEM and thus is reported by the liquid crystal.

EXAMPLE 11

Formation of PEMs of Hyaluranon (HA) and Collagen (COL) on LCs

This example describes the formation of PEMs from COL and HA on the interfaces of LCs. HA, also called hyaluronic acid, is a polysaccharide extracellular matrix (ECM) molecule abundant in tissues, and tight regulation on its synthesis controls cell adhesion and motility during cancer metastasis, stem cell homing, wound healing, etc. Collagen is a predominant ECM protein as well. To prepare PEMs of (HA/COL) of order “n”, with n representing the number of adsorbed layer pairs, HA and COL solutions are prepared as follows. Collagen of 1 mg/ml in acetic acid (Sigma, St. Louis, Mo.) is diluted to 0.2 mg/ml with water. Hyaluronan (MW=400 KDa, Barcelona, Spain) is dissolved in pure water at 1 mg/ml. Both solutions are adjusted to pH 4 with HCl. Between each adsorption step, the films are extensively rinsed with $10^{-4}$M HCl. To characterize growth of the PEM, the collagen stock is dialyzed to concentrate the collagen. Dialysis removes salts that may interfere with the labeling reaction. The concentrated collagen is adjusted to 8 mg/ml and pH 8.3 for the labeling reaction with Alexa430-conjugated succinimidyl ester. This ester reacts with unprotonated amine. The ester solution is prepared in anhydrous DMSO with a 1:20 ratio to amount of collagen. Free ester is hydrolyzed in about 24 hours. The reaction mixture is incubated at room temperature for an hour before it is ready to be diluted and deposited on HA. Fluorescence intensity is approximately proportional to PEM thickness, a relationship shown in previously published data.

EXAMPLE 12

PEMs Formed on LCs can be Used to Report Specific Binding Events Between Proteins PEMs of HA and COL are prepared on LCs, as described in the examples above. The optical appearance of the LC is determined by using polarized light microscopy and a birefringence mapper. Following formation of the PEMs, anti-collagen antibodies (1 micromolar) at added to the aqueous phases. A change in optical appearance of the LC reports the presence of the antibodies. In contrast, when anti-biotin antibodies are introduced into the aqueous phase there is no change in optical appearance of the LC. This example serves to illustrate the way in which PEMs formed on LCs can be used to report specific binding events between proteins.

EXAMPLE 13

Formation of PEMs Containing Biomolecules on LC Emulsion Droplets

PEMs on LC droplets are useful systems for drug delivery and provide biophysical models of cells. In this example, LC emulsions (i.e., particles made of LCs dispersed in water) will be used as templates for the deposition of PEMs. A distinct advantage offered by emulsions is (i) their large surface area, potentially offering orders of magnitude greater sensitivity for recording molecular interactions with the LC interface; and (ii) the prospect of forming mobile and passive optical reporters of the presence of targeted chemical and biological species, and (iii) the opportunity to further engineer these systems through the distortions and defects formed by LCs in confined, spherical geometries. Such materials might find use, for example, as "smart colloids" capable of reporting biological activity (e.g., BoNT/A) when added to a sample or incorporated into a coating.

In this example, PEMs of HA and COL are prepared on LC emulsion droplets, as described in the examples above. The optical appearance of the LC is determined by using polarized light microscopy and a birefringence mapper. Following formation of the PEMs, anti-collagen antibodies (1 micromolar) at added to the aqueous phases. A change in optical appearance of the LC reports the presence of the antibodies. In contrast, when anti-biotin antibodies are introduced into the aqueous phase there is no change in optical appearance of the LC emulsion droplets. This example serves to illustrate the way in which PEMs formed on LC emulsion droplets can be used to report specific binding events between proteins.

EXAMPLE 14

PEM Coating of Emulsions

In this example, the formation of polyelectrolyte multilayers on thermotropic LC (oil)-in-water emulsions is described. The growth of the poly(styrene sulfonate) (PSS)/poly(allylamine hydrochloride) (PAH) multilayers was characterized with microelectrophoresis, flow cytometry, and fluorescence microscopy. Up to eight PSS/PAH bilayers were deposited and the effect of the multilayer formation on the orientation of the LC was examined using polarized light microscopy. The inventors also examined the influence of the multilayer coating on the interaction between an analyte (surfactant) and the LC core. The PSS/PAH-coated LC droplets were subsequently treated with ethanol to dissolve the LC cores to form hollow capsules. The production of stable capsules confirmed the growth of the multilayer films, and the integrity of the film formed. These results are significant in that (a) they demonstrate the ability to prepare stable LC emulsions with an easily modifiable interface, and (b) they show that LC emulsions can be used to template polyelectrolyte multilayer formation. These developments are significant because of the potential benefits in sensing and encapsulation applications.

Emulsion Preparation. The LC-in-water emulsions were formed by sonicating a mixture of 1 vol. % 5CB in a dispersant at 10 W for 60 s. Three types of dispersants were used: (a) water, (b) an aqueous solution of a strongly charged polyelectrolyte, poly(styrene sulfonate) (PSS) (1 mg $mL^{-1}$), and (c) an aqueous solution of a cationic phospholipid, 1,2-dilauroyl-sn-glycero-3-ethylphosphocholine (DLEPC) (700 μM). The resulting emulsions were denoted as 5CB-$H_2O$, 5CB-PSS and 5CB-DLEPC, respectively. The LC droplets in all three types of emulsions were spherical, with a size range of 1-10 μm and were visually observed to be stable against coalescence for months. The 5CB-PSS and 5CB-DLEPC emulsions are stable as PSS and DLEPC can associate with the interface of the water-immiscible droplets of 5CB, effectively acting like surfactants, electrostatically stabilizing the droplets.

Figure 21:
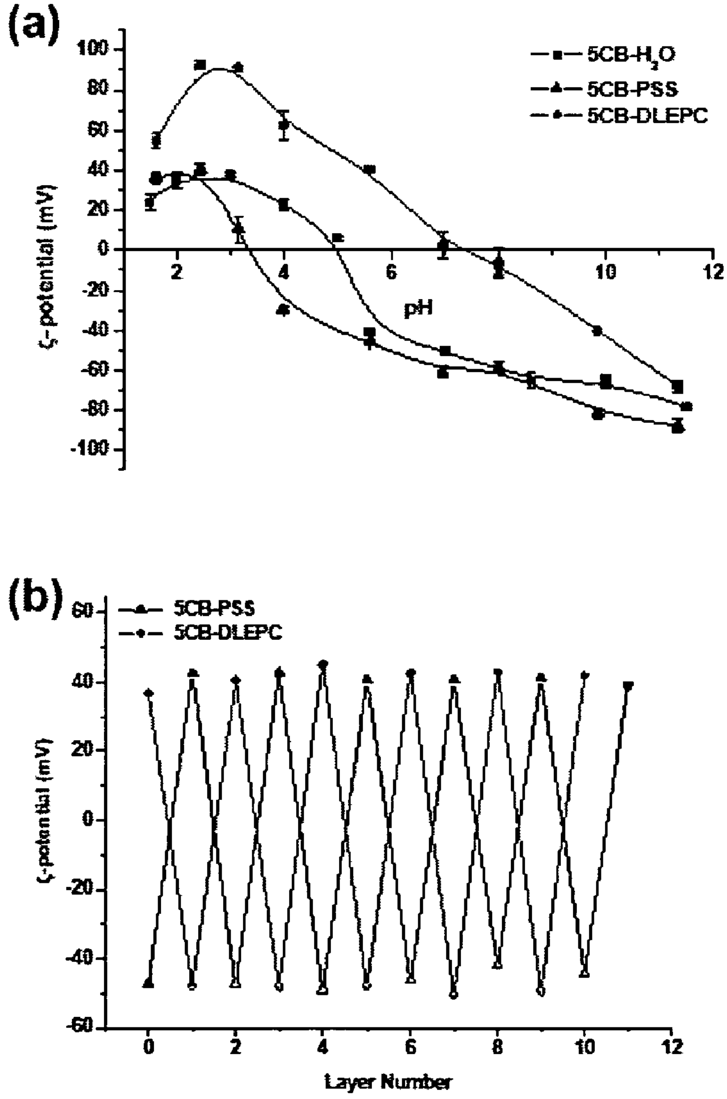
FIG. 21. (a) pH dependence of the ζ-potential of uncoated LC emulsions. (b) ζ-potential of (PAH/PSS)-coated 5CB-PSS and 5CB-DLEPC emulsions as a function of layer number. The ζ-potential measurements were taken in water (pH ~5.7). Hollow and filled symbols indicate the PSS and PAH adsorption steps, respectively. The error in ζ-potential measurements is ±5 mV.

The ζ-potentials of 5CB-$H_2O$, 5CB-PSS and 5CB-DLEPC droplets were −40 mV, −45 mV and +40 mV as prepared. (measured in water at pH ~5.7). The ζ-potentials were also measured over a wide pH range to determine the isoelectric point (IEP) of the droplets. The IEP for the 5CB-$H_2O$ droplets was found to be 5, and the IEP shifted to 3.5 and 7.0 for the 5CB-PSS and 5CB-DLEPC droplets, respectively (FIG. 21*a*). This is indicative of the PSS and DLEPC providing charge stabilization for the emulsions. Notably, 5CB did not form a stable emulsion in water when PAH was used instead of PSS. This result is similar to previous findings; PSS can render uncharged pyrene water-dispersible, but PAH does not. This result suggests that successful emulsification of 5CB with PSS may be attributed to the amphiphilic nature of PSS (the aromatic group is hydrophobic while the charged sulfonate group is hydrophilic) and/or the π-π interactions between the phenyl groups of 5CB and PSS.

The stability of the 5CB-$H_2O$ emulsion is likely due to the spontaneous adsorption of hydroxide ions at the oil-water interface, which has been reported for surfactant-free emulsions of linear alkanes such as hexadecane and dodecane. In those studies, the oil droplets were negatively charged and the magnitude of their ζ-potential depended on the pH and the ionic strength of the aqueous phase. This phenomenon has been reported to be specific to the hydroxide ion; other cations and anions are not preferentially adsorbed at the oil-water interface. This specificity has led to the suggestion that adsorption of the hydroxide ion may involve hydrogen bonding with the water molecules at the interface. The 5CB-$H_2O$ emulsion exhibits a similar behavior; it is negatively charged as prepared (−40 mV, measured in water at pH ~5.7), and this charge is pH-dependent. The IEP the 5CB-$H_2O$ emulsion is 5, which is slightly higher than those reported for oil-in-water emulsions of linear alkanes (IEP ca. 3-4).

Multilayer Coating of Emulsions. The polyelectrolytes for LbL assembly were deposited from 1 mg $mL^{-1}$ solutions containing 0.1 M NaCl. The electrolyte is added to facilitate polyelectrolyte adsorption. In the absence of salt, the polyelectrolytes adopt a stretched conformation and adsorb as thinner, more rigid layers, which might result in incomplete and/or less homogeneous coverage of the LC droplets. The pH of the PAH solution was adjusted to pH 7 ($pK_a$ of PAH is ~8.5) while the pH of the PSS solution was not adjusted (PSS is a strong polyelectrolyte). The 5CB-$H_2O$ emulsions were negatively charged as prepared; hence the cationic PAH was deposited as the first layer. Despite the stability of the 5CB-$H_2O$ emulsions, the LbL assembly with PAH and PSS did not proceed as well as with the 5CB-DLEPC or 5CB-PSS emulsions. ζ-potential measurements of these samples show inconsistent magnitudes and a broad distribution of charges (data not shown). Flow cytometry was also used to quantify the fluorescence intensity of the 5CB-$H_2O$ emulsion droplets after alternating adsorption of fluorescein isothiocyanate-labeled PAH (PAH-FITC) and PSS. Although there was a general increase in fluorescence intensity over 14 adsorption steps, the intensity was less than half of that observed with 5CB-PSS and 5CB-DLEPC emulsions. The inventors also observed desorption of PAH-FITC after coating; the fluorescence measured in the aqueous phase of 5CB-$H_2O$ emulsions with a PAH-FITC terminated layer slowly increased after the adsorption and washing steps. These results indicate that PAH-FITC was weakly bound to the 5CB-$H_2O$ core, resulting in incomplete polymer coverage of the droplets and the surface of these droplets having both positive and negative charges, accounting for the poorer stability of these emulsions.

On the other hand, the 5CB-PSS and 5CB-DLEPC emulsions were coated successfully with at least 16 layers of PAH and PSS. The alternating ζ-potentials for both the 5CB-PSS and 5CB-DLEPC emulsions during LbL assembly (between +40 mV and −50 mV) are consistent with stepwise adsorption of cationic PAH and anionic PSS (FIG. 21*b*). These values are similar to ζ-potentials of PSS and PAH alternately deposited on charged solid particles. As each layer is adsorbed, the surface charge is reversed, allowing the adsorption of the next layer via electrostatic interactions.

Figure 22:
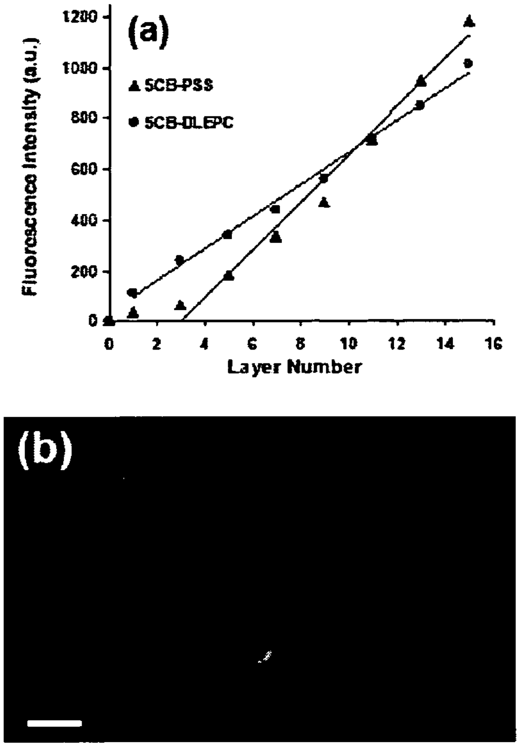
FIG. 22. (a) Fluorescence intensity of (PAH-FITC/PSS)-coated 5CB-PSS and 5CB-DLEPC emulsions as a function of layer number, as measured by flow cytometry. The measurements were taken after deposition of every bilayer (after every PAH-FITC layer). (b) Fluorescence image of the 5CB-PSS emulsion coated with seven bilayers of PAH-FITC/PSS. Scale bar is 10 μm.

However, ζ-potential measurements only serve as a qualitative indication of multilayer growth. As such, PAH-FITC was used to further confirm multilayer growth on 5CB-PSS and 5CB-DLEPC emulsions using flow cytometry. The increase in fluorescence intensity of the droplets was quantified using flow cytometry (FIG. 22*a*). The growth in fluorescence intensity was linear after the third and first layer for 5CB-PSS and 5CB-DLEPC emulsions, respectively. The thinner initial layers for the 5CB-PSS system indicate that it takes a few deposition steps for the layer thickness to reach an equilibrium value. This can be explained by substrate effects, which are commonly observed in the first few layers in LbL systems. A fluorescence image of 5CB-PSS coated with seven bilayers of PAH-FITC/PSS shows uniform fluorescence around the droplets, confirming the flow cytometry results (FIG. 22*b*). Similar images were obtained for 5CB-DLEPC emulsions coated with seven bilayers of PSS/PAH-FITC (data not shown). The results obtained from microelectrophoresis, flow cytometry, and fluorescence microscopy all demonstrate that PE multilayer growth at the mobile interface of 5CB emulsion droplets is comparable to similar multilayers assembled on solid, charged colloidal particles.

Figure 23:
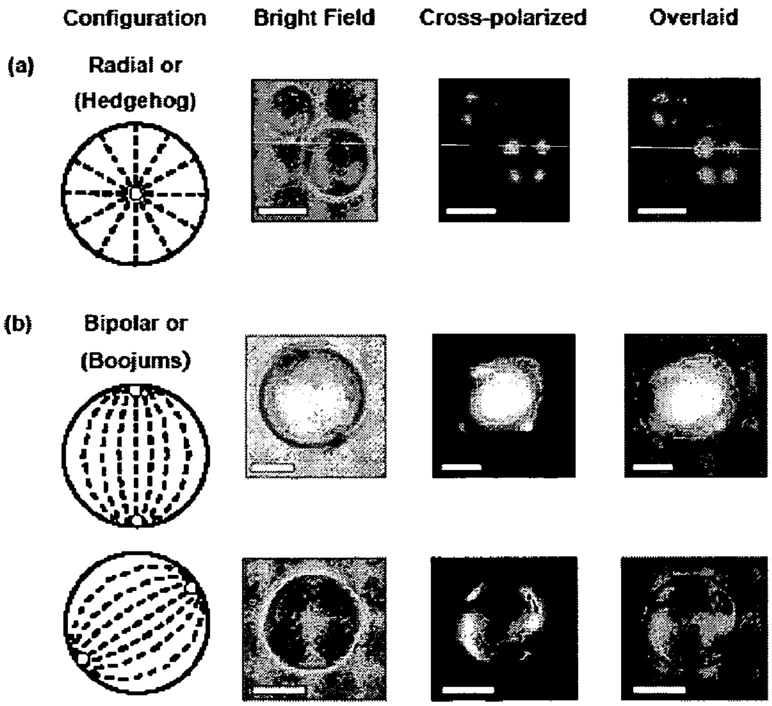
FIG. 23. Director profiles and optical microcopy images of (a) 5CB-H2O emulsions and (b) 5CBDLEPC emulsions. Scale bars are 2 μm.
Figure 24:
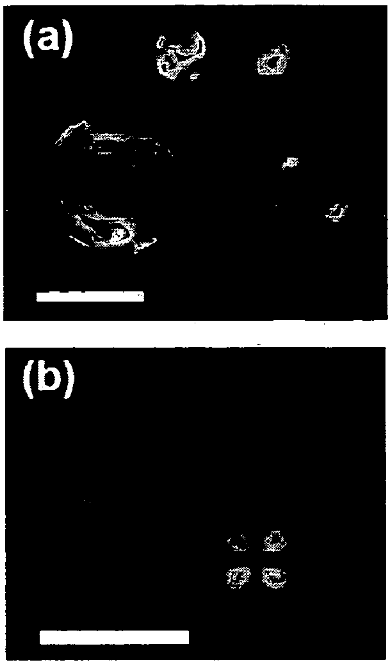
FIG. 24. Cross-polarized images of (a) 5CB-PSS emulsions coated with (PAH/PSS)5 and (b) 5CBDLEPC emulsions coated with (PSS/PAH)5. Scale bars are 5 μm.

Orientation of 5CB in the Emulsions. Polarized microscopy was used to study the orientation of the 5CB at the droplet interface before and after deposition of the multilayer films. Past studies have established that the orientations of a LC within a droplet depend on factors such as the bulk elasticity of the LC, the orientation of the easy axis of the LC at the interface of the droplet, and the anchoring energy of the LC. For sufficiently large droplets, surface anchoring dominates, which results in droplets that contain topological defects at equilibrium. The inventors observed the orientation of 5CB in the emulsion droplets to be independent of droplet size. This implies that the droplets are at the limit of strong anchoring. Previous studies have also shown that planar anchoring of 5CB at the interface results in a bipolar configuration where each droplet contains two or more point defects at the interface, known as 'boojums'. On the other hand, homeotropic anchoring of 5CB at the interface results in a radial configuration, where each droplet has a point defect at its center, known as a 'hedgehog'. Optical images (crossed polars) of 5CB-H2O and 5CB-DLPC emulsion droplets are shown in FIG. 23 along with the orientations of the 5CB within the droplets. The 5CB-$H_2O$ emulsion droplets have a bipolar configuration with two point defects at the surface, while the 5CB-DLEPC emulsion droplets have a radial configuration, with characteristic cross-like appearances. The appearance of the 5CB-PSS emulsion droplets was similar to the 5CB-H2O droplets. The orientations of the LC at the interfaces of the droplets are similar to the orientations of 5CB and DLEPC-decorated 5CB reported previously at planar LC-aqueous interfaces. FIG. 24 shows optical images (crossed polars) of 5CB-PSS and 5CB-DLEPC emulsion droplets coated with 5 bilayers of PAH/PSS. The results reveal that the bipolar and radial configurations of LC within the 5CB-PSS and 5CB-DLEPC emulsion droplets are preserved during multilayer coating.

Figure 25:
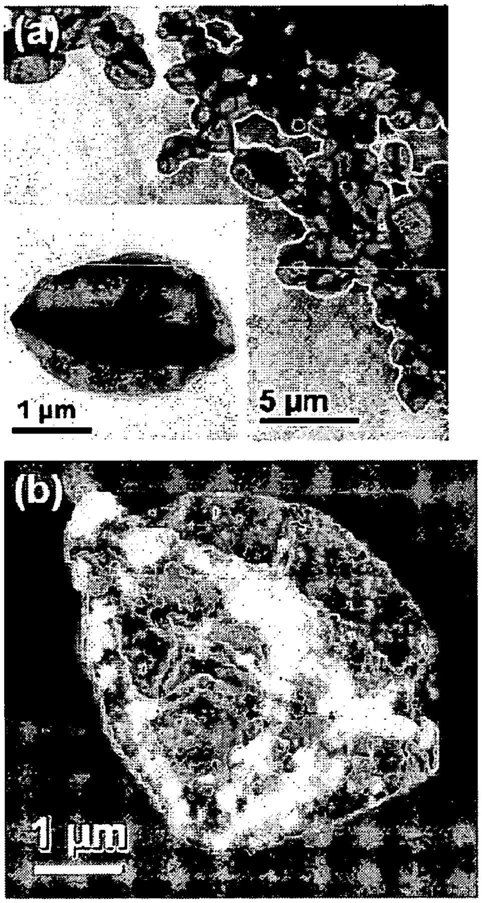
FIG. 25. (a) TEM images of hollow capsules obtained from 5CB-PSS emulsions coated with (PAH/PSS)5 and (b) an AFM image of a hollow capsule obtained from 5CB-DLEPC emulsions coated with (PSS/PAH)5/PSS. Z-scale: 245 nm.

Effect of surfactants on the Orientation of 5CB in the Emulsions. In previous studies, the exposure of 5CB to surfactants such as sodium dodecyl sulfate (SDS, anionic) caused a rapid ordering transition from a planar to a homeotropic orientation of 5CB. Preliminary studies on the uncoated and $(PAH/PSS)_7$-coated emulsions showed that exposure to 5 mM SDS triggered an ordering transition of 5CB from a planar to a homeotropic orientation. This was reflected by the appearance of crosses on the emulsion droplets when viewed with cross-polarizers (FIG. 25). The ordering of 5CB in the uncoated emulsions changed from planar to homeotropic instantaneously, however this change took about five min to occur for the $(PAH/PSS)_7$-coated emulsions. This result indicates that SDS can permeate the multilayer through to the LC core. In addition, the multilayer can influence the way SDS penetrates and adsorbs at the 5CB interface by slowing the diffusion kinetics.

Hollow Capsules. To further verify the structural integrity of the multilayer coating on LC emulsions, the inventors selectively removed the LC core of the multilayer-coated emulsion droplets by dissolution of the LC with ethanol to yield hollow polyelectrolyte capsules. The inventors found that hollow capsules could only be obtained from multilayer-coated emulsions with a PSS terminated layer. Emulsions coated with a PAH terminated layer aggregated upon treatment with ethanol. It is possible that the ionization of PAH at the surface decreases (via conversion of the ammonium groups to amines) when exposed to ethanol, thereby destabilizing the emulsion. Decreasing solvent polarity (e.g. increasing ethanol content) of the PAH deposition solutions can result in a dramatic increase of layer thickness as a consequence of charge screening and the polyelectrolytes adopting a more coiled conformation. The PSS-terminated multilayer-coated emulsions turned clear immediately after the addition of ethanol. This is a common indication of core dissolution in other multilayer systems where solid core particles are used.

Figure 26:
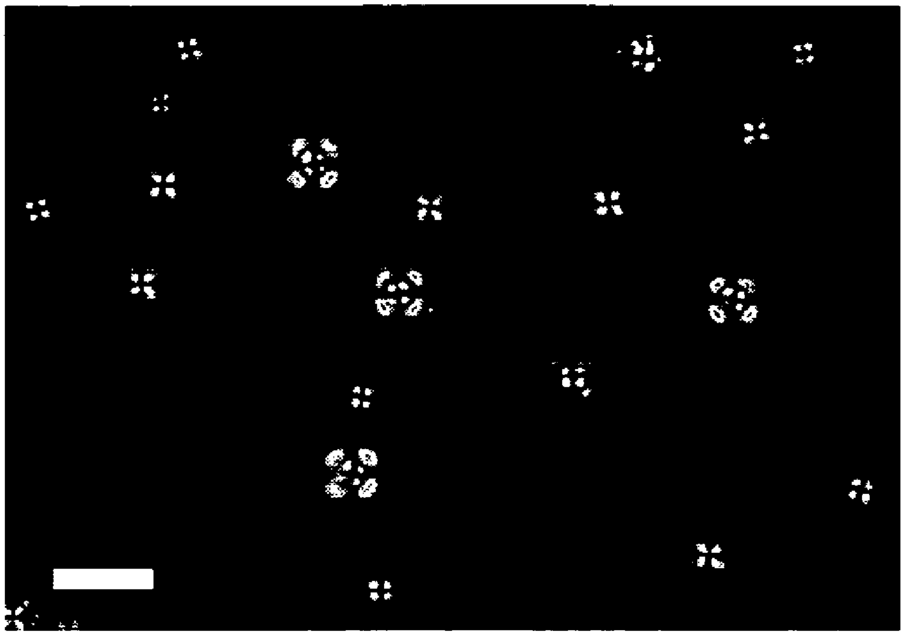
FIG. 26. Cross-polarized images of 5CB-PSS emulsions coated with (PAH/PSS)7 after exposure to 5 mM SDS. Scale bar is 10 μm.

The hollow capsules were characterized with transmission electron microscopy (TEM) and atomic force microscopy (AFM). The capsule walls have a grainy texture, which is probably due to slight rearrangement of polyelectrolytes when they were exposed to ethanol. When dried, the capsules collapse and the folds are visible from TEM and AFM images (FIG. 26). AFM was used to obtain the thickness of the capsule walls by taking a cross-sectional profile of the capsules where it was folded only once. Hence, the measured thickness corresponds to twice the multilayer wall thickness. The average thickness per layer was determined by taking the average thickness of several cross-sectional profiles and dividing by twice the total number of layers deposited. The layer thickness was calculated to be approximately 1.4 nm for both multilayer-coated 5CB-PSS and 5CB-DLEPC emulsions, which corresponds well to typical layer thickness of the same polyelectrolyte multilayers assembled on planar and colloidal supports. This study also demonstrates that thermotropic LCs, despite having a mobile interface, can be used as cores in core-shell systems. The ability to synthesize monodisperse emulsions at a desired size overcomes difficulties currently faced when using solid particles as templates of polyelectrolyte capsules. For example, it is often difficult to completely remove melamine formaldehyde (MF) cores; some residual MF may remain in the capsule walls.

Experimental Section.

Materials. Poly(sodium-4-styrenesulfonate) (PSS, $M_w$, 70 kDa), poly(allylamine hydrochloride) (PAH, $M_w$, 70 kDa), and sodium dodecyl sulfate (SDS) were purchased from Sigma-Aldrich and used without further purification. Fluorescein isothiocyanate-labeled PAH (PAH-FITC) was prepared as described previously. The nematic liquid crystal 4'-pentyl-4-cyanobiphenyl (5CB) was purchased from EMD Chemicals (Hawthorne, N.Y.) and used without further purification. The phospholipid 1,2-dilauroyl-sn-glycero-3-ethylphosphocholine (DLEPC) was obtained from Avanti Polar Lipids (Alabaster, Ala.). An inline Millipore RiOs/Origin system was used to produce high-purity water with a resistivity greater than 18.2 MΩ·cm.

Emulsion Preparation. The LC emulsions (1 vol. %) (typically 1 mL) were formed by mixing 10 μL of 5CB with 1 mL of dispersant with a tip sonicator at a power of 10 W for 60 s. Three types of dispersants were used: 1) water, 2) aqueous solution of PSS (1 mg $mL^{-1}$, no added salt), and 3) aqueous solution of DLEPC (700 μM).

Microelectrophoresis. ζ-potentials were measured using a Malvern Zetasizer2000 instrument. Approximately 2 μL of 1 vol. % emulsions was added to 3.5 mL of water. The quoted values were calculated by taking the average of 5 successive measurements. The pH of water was adjusted by adding NaOH or HCl no more than 5 min before measurement.

Multilayer Coating of Emulsions. 5CB-PSS and 5CB-DLEPC emulsions were first washed 3 times with water. Approximately 1 mL of emulsion and 1 mL of water was added to a 2 mL Eppendorf tube. The tube was agitated with a vortex mixer and then centrifuged at 5000 g for 5 min. This resulted in a pellet forming at the bottom of the tube. Approximately 1 mL of the supernatant was removed and replaced with water. This was repeated twice to remove excess PSS and DLEPC prior to polyelectrolyte coating. The PAH and PSS solutions for LbL were made to 1 mg $mL^{-1}$ containing 0.1 M NaCl and PAH-FITC was made to 0.5 mg $mL^{-1}$ containing 0.1 M NaCl. After washing, 1 ml of polyelectrolyte solution was added to 1 mL of the emulsion. The mixture was agitated with a vortex mixer and allowed to incubate for 15 min. After adsorption, the dispersions were centrifuged (at 5000 g, 5 min), after which the supernatant was removed and replaced by water. Washing was performed 3 times, followed by adsorption of the next polyelectrolyte. The entire process was repeated until the desired number of layers was achieved. The initial 5CB-PSS emulsion is negatively charged (as determined from ζ-potential measurement), so the first polyelectrolyte adsorbed is PAH. Conversely, since 5CB-DLEPC emulsion is positively charged, the first layer deposited was PSS.

Flow Cytometry. Fluorescence measurements of the (PAH-FITC/PSS)-coated LC emulsions were carried out using a Becton Dickinson FACS Calibur flow cytometer. 1 μL of 1 vol. % emulsion was diluted with 200 μL of water and this solution was analyzed on the instrument. Measurements were acquired with triggering on the forward scatter detection (E0 detector) with a threshold of 400. FITC fluorescence was monitored on the FL1 (515-545 nm) parameter with a PMT voltage of 550 V. For each sample, 30,000 particles were analyzed at a rate of approximately 500 particles per second. For each incubation time, a background sample was recorded (i.e., the same sample before any polyelectrolyte coating). This signal was subtracted from the signal of the particles coated with a different number of fluorescent layer. Flow cytometry data analysis was performed with Summit v. 3.1 (Cytomation, Inc., Colorado, USA). A sub-population was analyzed by applying a gate within the entire population to exclude particle aggregates and the same gate was used for one set of samples with different layer numbers. The mean fluorescence intensity was obtained from the fluorescence intensity histograms.

Polarized and Fluorescence Microscopy. The orientation of the LC within droplets was examined with plane-polarized light in transmission mode on an Olympus IX 71 inverted fluorescence microscope with crossed polarizers. Fluorescence images were taken using the same microscope with a FITC filter cube. In both cases, a 60× oil immersion objective was used and images were captured with a color camera.

Preparation of Hollow Capsules. Multilayer-coated 5CB-PSS and 5CB-DLEPC emulsions with an outermost PSS layer were treated with ethanol. Approximately 1 mL of ethanol was added to ~1 mL of emulsion and the mixture was agitated with a vortex mixer and allowed to stand for 15 min. The mixture was then centrifuged, the supernatant removed and fresh ethanol was added. This was repeated three more times. After the last ethanol addition, the samples were allowed to stand overnight to ensure complete dissolution and removal of 5CB. Before characterization, the hollow capsules were washed three times with water. Air-dried hollow capsules were characterized with a Philips CM120 BioTWIN transmission electron microscope (TEM) operated at 120 kV and a Nanoscope IIIa atomic force microscope (AFM) (Digital Instruments Inc., Santa Barbara, Calif.) operated in Tapping Mode™ using silicon cantilevers with a resonance frequency of ca. 290 kHz (MikroMasch, USA). Image processing (first-order flattening) was carried out with Nanoscope 4.43r8 software.

Those skilled in the art will recognize, or be able to ascertain using no more than routine experimentation, numerous equivalents to the specific materials and methods described herein. Such equivalents are considered to be within the scope of this invention and encompassed by the following claims.

What is claimed is:

1. A method for providing a polyelectrolyte multilayer film at a liquid-liquid interface, comprising steps of sequentially-depositing layers of anionic and cationic polyelectrolytes at a liquid-liquid interface that is formed between immiscible first and second liquids, wherein the first liquid is an aqueous solution and the second liquid is a liquid crystal, whereby a polyelectrolyte multilayer film is provided at said liquid-liquid interface.

2. The method according to claim 1 wherein the liquid crystal is in the form of a droplet.

3. The method according to claim 1 wherein the second liquid is in the form of a droplet.

4. A method for providing a polyelectrolyte multilayer film at an aqueous-liquid crystal interface, comprising steps of sequentially-depositing layers of cationic and anionic polyelectrolytes at an aqueous-liquid crystal interface that is formed between an aqueous phase and a liquid crystal phase whereby a polyelectrolyte multilayer film is provided at said aqueous-liquid crystal interface.

5. The method according to claim 4 wherein the polyelectrolyte multilayer film is capable of interacting with an analyte present in the aqueous solution thereby causing a change in orientation or ordering of the liquid crystal.

6. The method according to claim 4 wherein the polyelectrolyte multilayer film includes an excipient capable of interacting with an analyte present in the aqueous solution thereby causing a change in orientation or ordering of the liquid crystal.

7. The method according to claim 6 wherein said excipient is a ligand or a receptor capable of selectively-binding said analyte, an enzyme capable of catalyzing a transformation of the analyte, a molecule capable of undergoing a chemical reaction in the presence of the analyte, or an enzyme substrate capable of being transformed by said analyte.

8. The method according to claim 4 wherein the polyelectrolyte multilayer film is deposited directly on the liquid crystal phase.

9. A method for providing an unsupported polyelectrolyte multilayer film comprising steps of:

(a) providing a liquid-liquid interface between immiscible first and second liquids, wherein the first liquid is an aqueous solution and the second liquid is a liquid crystal;

(b) sequentially-depositing layers of cationic and anionic polyelectrolytes at the liquid-liquid interface whereby a polyelectrolyte multilayer film is provided at the liquid-liquid interface; and (c) removing the first and second liquids to provide an unsupported polyelectrolyte multilayer film.

10. The method according to claim 9 wherein the second liquid is in the form of a droplet.

11. The method according to claim 9 wherein the unsupported polyelectrolyte multilayer film is in the form of a hollow capsule.

* * * * *